(12) United States Patent
Martini et al.

(10) Patent No.: US 9,261,452 B2
(45) Date of Patent: Feb. 16, 2016

(54) FLOW CYTOMETER

(71) Applicant: Palo Alto Research Center Incorporated, Palo Alto, CA (US)

(72) Inventors: Joerg Martini, San Francisco, CA (US); Noble M. Johnson, Menlo Park, CA (US); Michael I. Recht, Mountain View, CA (US); David M. Johnson, San Francisco, CA (US); Tim Curley, San Carlos, CA (US); Peter Kiesel, Palo Alto, CA (US); Martin Sheridan, Redwood City, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 67 days.

(21) Appl. No.: 14/139,246

(22) Filed: Dec. 23, 2013

(65) Prior Publication Data
US 2015/0177119 A1    Jun. 25, 2015

(51) Int. Cl.
*G01N 21/00* (2006.01)
*G01N 15/14* (2006.01)

(52) U.S. Cl.
CPC ........ *G01N 15/1459* (2013.01); *G01N 15/1436* (2013.01); *G01N 2015/1447* (2013.01)

(58) Field of Classification Search
CPC ......... G01N 12/00; G01N 33/00; G01N 1/00; G01N 15/00; B01L 3/00; C12Q 1/00; G01F 1/00
USPC .................. 356/440, 344, 436, 446, 318, 369
See application file for complete search history.

(56) References Cited

U.S. PATENT DOCUMENTS

| 4,251,733 | A | 2/1981 | Hireleman, Jr. | |
| 5,422,712 | A * | 6/1995 | Ogino | 356/73 |
| 5,444,527 | A * | 8/1995 | Kosaka | 356/73 |
| 7,262,838 | B2 * | 8/2007 | Fritz | 356/73 |
| 7,540,205 | B2 | 6/2009 | Nelson et al. | |
| 7,688,427 | B2 * | 3/2010 | Cox et al. | 356/39 |
| 8,122,779 | B2 | 2/2012 | Nelson et al. | |
| 8,263,955 | B2 | 9/2012 | Kiesel et al. | |
| 8,373,860 | B2 | 2/2013 | Kiesel et al. | |
| 8,435,738 | B2 | 5/2013 | Holmes et al. | |
| 8,475,739 | B2 | 7/2013 | Holmes et al. | |
| 8,512,650 | B2 | 8/2013 | Jungheim et al. | |
| 8,518,345 | B2 | 8/2013 | Butz et al. | |
| 8,524,170 | B2 | 9/2013 | Petrek | |
| 2008/0181827 | A1 | 7/2008 | Bassler et al. | |
| 2008/0183418 | A1 | 7/2008 | Bassler et al. | |
| 2010/0167412 | A1 | 7/2010 | Xiao et al. | |
| 2010/0288941 | A1 | 11/2010 | Ayliffe et al. | |
| 2011/0076205 | A1 | 3/2011 | Kelly et al. | |
| 2011/0222062 | A1 | 9/2011 | Martini et al. | |
| 2011/0291025 | A1 * | 12/2011 | Fortin et al. | 250/458.1 |

(Continued)

FOREIGN PATENT DOCUMENTS

WO    WO2013/085797    6/2013

*Primary Examiner* — Tarifur Chowdhury
*Assistant Examiner* — Isiaka Akanbi
(74) *Attorney, Agent, or Firm* — Hollingsworth Davis, LLC

(57) ABSTRACT

Embodiments are directed to a host structure that includes a waveguide configured to deliver measurement light to a compartment at least partially within the host structure. The compartment is configured to reversibly engage a fluidic optical cartridge. The host structure also includes a detector configured to receive and process output light emanating from the fluidic optical cartridge as well as electronics to process signals from the detector.

27 Claims, 28 Drawing Sheets

(56) References Cited

U.S. PATENT DOCUMENTS

| | | | |
|---|---|---|---|
| 2012/0196314 A1* | 8/2012 | Nawaz et al. | 435/29 |
| 2013/0037726 A1 | 2/2013 | Kiesel et al. | |
| 2013/0037728 A1 | 2/2013 | Kiesel et al. | |
| 2013/0078625 A1 | 3/2013 | Holmes et al. | |

* cited by examiner

FLOW CYTOMETER

TECHNICAL FIELD

Embodiments are directed to a fluidic optical cartridge reversibly engaged with a host structure useful as a flow cytometer.

BACKGROUND

The present disclosure relates generally to articles and methods that involve light emanating from objects as they travel through a fluidic channel. Various techniques have been proposed for analyzing light emanating from objects. One such technique describes a fluidic structure with a channel along which is at least one sensing component that can obtain information about objects traveling within the channel, such as droplets or other particulates carried by fluid. A sensing component includes one or more detectors that can detect a range of photon energies that emanate from the objects. A processor can receive information about the objects from the sensing components and use the received information to obtain spectral information. Analyzers with time variation based on coded spatial modulation have also been disclosed.

Flow cytometers have been developed that can utilize light emanating from objects, for example, biological particles, to determine particle size and to identify component particles in fluids such as, for example blood. Typically, the fluid is obtained from a living specimen and then is analyzed in a laboratory by a flow cytometer. Many such flow cytometers are known and are commercially available but most of these flow cytometers are not useful for point-of-use applications.

SUMMARY

Embodiments are directed to a host structure. The host structure includes a compartment disposed at least partially within the host structure, the compartment being configured to reversibly engage with a fluidic optical cartridge. The fluidic optical cartridge includes a fluidic structure that has a channel through which objects can travel along respective paths during operation of the apparatus. The channel has at least one transparent wall. The fluidic optical channel also includes at least one optical component configured to provide measurement light to the objects traveling through the channel, the output light emanating from the objects in response to the measurement light, the host structure further comprising a source of the measurement light. The host structure includes a waveguide configured to deliver measurement light to the compartment. The host structure also includes a detector configured to receive and process output light emanating from the fluidic optical cartridge and electronics to process signals from the detector. In some embodiments, the fluidic optical cartridge is engaged in the compartment of the host structure and forms a flow cytometer capable of analyzing objects in a fluid.

Other embodiments include a method that includes engaging a fluidic optical cartridge in a compartment of a host structure. The host structure includes a waveguide configured to deliver measurement light to a compartment at least partially within the host structure, the compartment being configured to reversibly engage a fluidic optical cartridge. The host structure also includes at least one detector configured to receive output light emanating from the compartment and to generate one or more electrical signals in response to the output light. Additionally, the host structure includes electronics configured to process the electrical signals. The fluidic optical cartridge includes a fluidic structure that includes a channel through which objects can travel along respective paths during operation of an apparatus, the channel having a transparent wall. The fluidic optical cartridge also includes optical components configured to provide measurement light to the objects traveling through the transparent channel. The method also includes drawing analyte fluid into the fluidic optical structure, measuring characteristic properties of the objects in the fluid based on the electrical signals, and dispensing the analyte fluid from the fluidic structure.

The above summary is not intended to describe each disclosed embodiment or every implementation of the present disclosure. The figures and the detailed description below more particularly exemplify illustrative embodiments.

BRIEF DESCRIPTION OF THE DRAWINGS

Throughout the specification reference is made to the appended drawings, where like reference numerals designate like elements, and wherein:

In the present disclosure:

FIG. 16A is an illustration of the parts in a waiting or "ready" mode. FIG. 16B is an illustration of the parts in a "measure" mode. FIG. 16C is an illustration of the parts in an "eject" mode.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
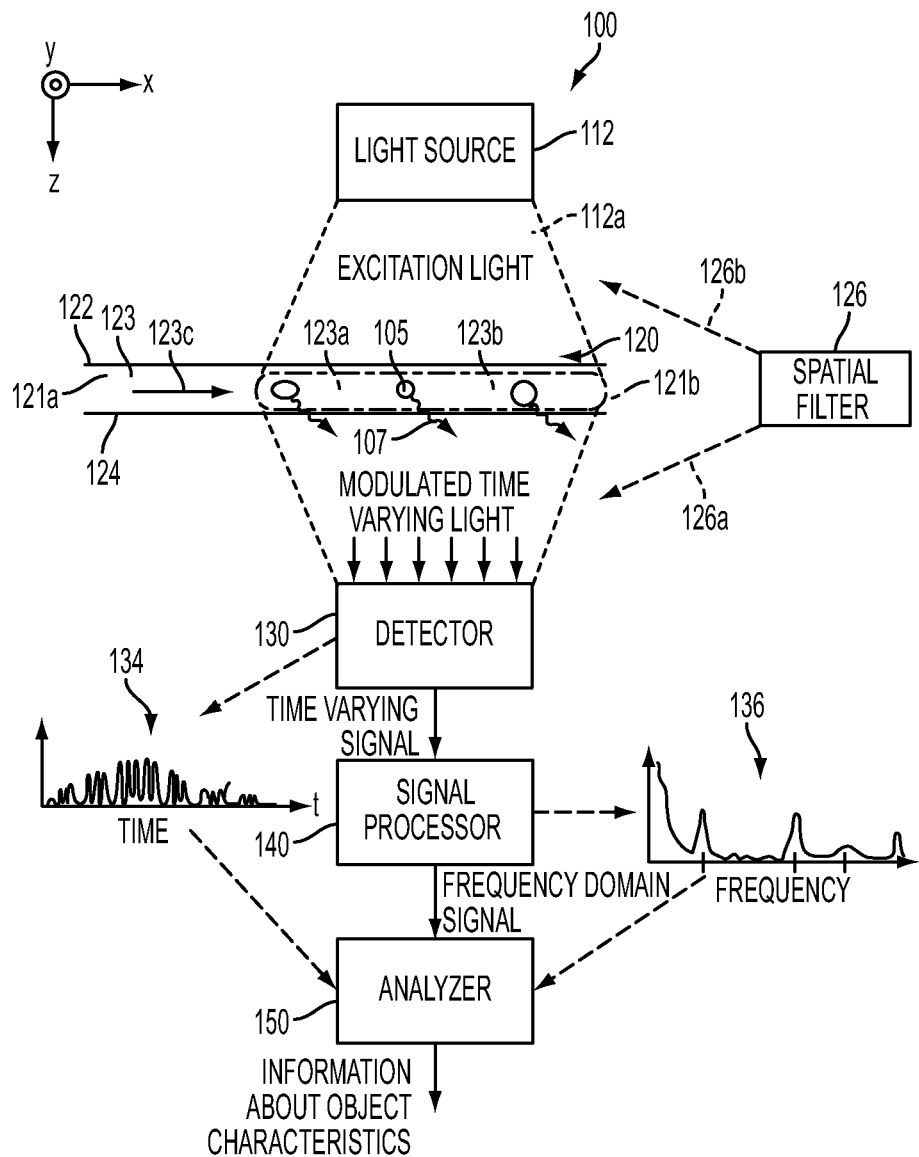
FIG. 1 is an example embodiment of an assembly with a spatial filter, detector, and analyzer configured to determine object characteristics based on spatially modulated light.

In the following description, reference is made to the accompanying set of drawings that form a part of the description hereof and in which are shown by way of illustration several specific embodiments. It is to be understood that other embodiments are contemplated and may be made without departing from the scope or spirit of the present invention. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all real numbers within that range (e.g. 1 to 5 includes 1, 1.5, 2, 2.75, 3, 3.80, 4, and 5) and any range within that range.

The strategic landscape for biological and biomedical testing and analysis is undergoing a transformation. Today, the majority of tests are performed at major, centralized clinical laboratories. This is in part because compact, robust, and inexpensive instruments for point of care (POC) testing are not available. Principal drivers for POC testing are reducing costs, obtaining timely test results, lowering mortality rates, and reducing morbidity. Commercial flow cytometers are sophisticated analytical instruments extensively used in research and clinical laboratories. They do not, however, meet the challenging practical requirements of POC testing. Additionally, laboratory flow cytometers require frequent cleaning or special provisions (e.g. sheath flow, acoustic focusing) to prevent cross contamination. Replacing the optical flow cell of a conventional flow cytometer is usually a labor intensive and expensive procedure.

In conventional flow cytometry, the size of the measurement area is restricted approximately to the size of the particle to be detected. In contrast, the apparatus and methods disclosed herein may use a much larger measurement region to increase the total flux of detected light that emanates from a particle of interest. In combination with the large measurement area, spatial filtering can be employed to enable a high spatial resolution in the micron range. This may allow for independently detecting and characterizing particles with a separation (in the flow direction) that can approach the dimension of individual particles. Also, the disclosed apparatus and methods can be intrinsically tolerant to background fluorescence originating from fluorescent components in solution, fluorescent components of the detection apparatus, and surface contaminants.

The disclosed device includes an apparatus or cartridge that can fit into a portable or hand-held host structure. In some embodiments, the host structure and the cartridge constitute a flow cytometer useful for point-of care testing. The cartridge can incorporate optics and fluid handling features of the cytometer and can be disposable. The cytometer can be used to analyze objects in a fluid, for example a biological fluid, at a point of care. The cytometer has a host structure that includes a compartment into which the disclosed apparatus can be reversibly engaged. The host structure can include one or more light sources, waveguides to deliver measurement light to the optics integrated into the cartridge, at least one detector to detect light emanating from the objects in the fluid to be analyzed and electronics to process and/or analyze electrical signals from the detector. The host structure may, optionally, include either a display and/or electronics configured to send information about the analysis to another external electronic device such as a computer, hand-held electronic device, or other electronic device by wire or wireless communication means. Details of a portable flow cytometer that includes the disclosed apparatus (fluidic optical cartridge) and a host structure can be found, for example, in Applicants' co-filed application, entitled "Fluidic Optical Cartridge", filed on the same day herewith. This co-filed application is herein incorporated by reference in its entirety.

Various techniques have been proposed for using light emanating from objects. These techniques have been functionalized for various applications and are generally effective for recognizing and obtaining object properties such as charge, porosity, surface characteristics, elasticity, and material composition for particular analytes. However, these techniques can be improved in order to lower fabrication costs while continuing to address the customer's desire for data processing that allows for real-time flow control. These criteria are can be addressed using spatially modulated emission techniques, such as those described herein, to extract object dimensions including a length with low-cost optics and detectors.

The embodiments described herein can be useful for analysis to determine the dimensional characteristics of an object in a flow direction. The dimensional characteristics determination can be based on spatially modulated light emanating from the object. In particular, the techniques can make use of a spatial mask that can be deployed in a variety of applications, including analysis of system properties and/or detection of various characteristics of analyte in a sample. In some implementations, a non-imaging photodetector can be used to generate a time varying electrical output signal based on the spatially modulated light allowing for better compatibility with high-throughput cytometry. Some characteristics of the objects can include their type, the speed that they travel through the cytometer, their color, and their size. The combined measurements of many objects can allow for a characterization of a sample of objects, for example, by determination of object (particle) concentration in the sample.

It will be understood that the techniques, apparatuses, systems, and methods described herein are applicable to detect various objects such as analytes or particles present in a sample. The term "object" refers broadly to any object of interest to be detected. In some applications, objects of interest are particles or analytes that are relatively small, and may be microscopic in size. However, the techniques can be broadly applicable to objects of any size or shape. A given particle or analyte may be or include one or a collection of biological cell(s), virus(es), macromolecule(s) (including certain proteins or protein chains, DNA or RNA fragments), molecules, droplets (e.g. oil in water), gas bubbles, microparticles, nanoparticles, and beads or other small particles that can bind and carry specific chemicals or other analytes.

In some embodiments, detectors can obtain information about objects by receiving signals from them, for example, signals in the form of light emanating from an object, whether through emission (e.g. radiation, fluorescence, incandescence, chemiluminescence, bioluminescence, other forms of luminescence, etc.), scattering (e.g. reflection, deflection, diffraction, refraction, etc.), or transmission, and can be sensed by a photodetector. Cells or other particles may be treated, e.g., stained or tagged with a suitable fluorescent probe or other agent, in such a way that they emit light or absorb light in a predictable fashion when illuminated with measurement light. In this regard, the light emitted by a given excited particle may be fluorescent in nature, or it may constitute a form of scattered light such as in the case of Raman scattering. For simplicity, the light that emanates from (by e.g., scattering, emission, or transmission) by an object is referred to herein as "emanating light" or "light emanating." It will be understood that the techniques, assemblies, apparatuses, systems, and methods described herein are applicable to detecting all forms of light emanating from an object or constituent parts thereof. In flow cytometry the biochemical selection of a (sub-)population of objects is often performed with fluorescent probes. For example, propidium iodide stains dead cells, while SYTO 9 stains live cells. Another example is DAPI which is known to stain cell nuclei.

FIG. 1 is an example of an assembly 100 configured to determine object characteristics based on spatially modulated light. Assembly 100 includes light source 112, spatial filter 126, a flow path, e.g., fluidic structure 120, detector 130, signal processor 140, and analyzer 150. Fluidic structure 120 is adapted to receive a sample of interest to be analyzed. The sample may enter the fluidic structure 120 at inlet 121a (that can be mated to, for example, an pipettor tip) and exit the fluidic structure 120 at outlet 121b, flowing generally along the x-direction through channel 123 formed between confining members 122 and 124 also referred to as "walls" (that can, in some embodiments, be opposite walls of a capillary tube). Channel 123 can have at least one transparent wall. Members 122, 124 may be or may comprise plates or sheets of glass, plastic, or other suitable transparent materials. Members 122 and 124 may or may not be planar in shape. For example, they may be portions of a unitary tube or pipe having a cross section that is circular, rectangular, or another shape. Other non-planar shapes are also contemplated. In some cases, confinement of the sample may not be necessary, whereupon one or both of members 122 and 124 may be omitted. At least a portion of confining member 122 is transmissive to measurement light emitted by the light source 112 at least in an excitation region 123a. In that regard, light source 112 may emit measurement light 112a towards fluidic structure 120.

In some cases, for example, light source 112 may include a conventional light-emitting diode (LED) source or a resonant cavity LED (RC-LED) source. If desired, the light source may incorporate one or more optical filters to narrow or otherwise tailor the spectrum of the resultant output light. Such optical filters can, for example, be bandpass filters. Whichever type of light source is selected, the spectral makeup or composition of the measurement light emitted by source 112 can be tailored to excite, to scatter, or otherwise to cause emanation of light from at least some of the objects that may be present in the sample, as discussed further below. Light source 112 may include a light-emitting diode, a superluminescent diode, a diode-pumped solid state laser, a frequency-doubled laser, a frequency-tripled laser, or even a frequency-quadrupled laser.

The sample is depicted as containing exemplary objects 105 of varying sizes and shapes. Objects 105 emanate light 107 in all directions (only some directions are illustrated). Objects 105 may have a variety of characteristics, some of which can be determined by analyzer 150 based on emanating light 107.

Detector 130 can receive time-varying light from objects 105 travelling in the channel as modulated by spatial filter 126 and can generate an electrical signal in response to the time varying light. The time variation in the light detected by detector 130 may be the result of interaction between the measurement light and an input spatial filter to create spatially patterned measurement light that illuminates object 105. Alternatively, the time variation in the light detected by detector 130 may be the result of interaction between light emanating from objects 105 and an output spatial filter as the objects travel through the channel along respective paths. In some embodiments, the detector includes an optical filter arranged between the detector and the objects. An optical filter can be particularly useful when the emanating light is fluorescent light and the optical filter is configured to substantially block the wavelengths of the measurement light and to substantially pass the wavelengths of the light emanating from the objects.

Assembly 100 of FIG. 1 includes spatial filter 126 (sometimes referred to as a mask) which can be positioned in various locations. The mask may be part of the fluidic device or may be part of a host structure. Dashed arrows 126a and 126b indicate possible locations of spatial filter 126 to provide spatially modulated light and/or modulated measurement light. In some configurations, indicated by arrow 126a, spatial filter 126 can be disposed between flow channel 123 and detector 130. In this position, spatial filter 126 is referred to as an output spatial mask. In other configurations, indicated by arrow 126b, the spatial filter 126 can be disposed between the light source 112 and the flow channel 123. In this position, spatial filter 126 is referred to as an input spatial filter. An input spatial filter may be adapted to transmit light emitted by the light source by varying amounts along excitation region 123a of flow channel 123. In this configuration, the input spatial filter creates patterned measurement light in excitation region 123a of flow channel 123. According to various implementations, an input spatial filter may comprise a physical mask including a sequence or pattern of first regions that are more light transmissive and second regions that are less light transmissive. The input spatial filter may alternatively or additionally comprise micro-optics or a patterned light source configured to create the excitation pattern. The excitation pattern can be imaged and/or directed onto excitation region 123a using optical components for the imaging (e.g., lenses) and/or direction, (e.g., fiber optics or waveguides).

In some embodiments, an output spatial filter may be utilized and disposed between objects 105 and detector 130 at detection region 123b of the flow channel. In some embodiments, excitation region 123a and detection region 123b overlap. In other embodiments, there may be partial overlap between the excitation and detection regions or the excitation and detection regions may be non-overlapping or multiple detection regions and/or excitation regions may be used with various overlapping and/or non-overlapping arrangements. In assembly 100 shown in FIG. 1, the output spatial filter may be adapted to interact with light 107 emanating from objects 105 in flow channel 123. In some embodiments, the output spatial filter may be a physical mask comprising a sequence or pattern of first regions that are more light transmissive and second regions that are less light transmissive. In some embodiments, color spatial filters may be used such that a first region of the color spatial filter is more transmissive to a first wavelength band and less transmissive to a second wavelength band and a second region of the color spatial filter is less transmissive to the first wavelength band and is more transmissive to the second wavelength band. Analyzers with time variation based on color-coded spatial modulation are disclosed, for example, in U.S. Pat. Appl. Publ. No. 2011/0222062 (Martini et al.).

According to some embodiments of assembly 100 that include the input spatial filter, as object 105 travels in flow direction 123c in excitation region 123a of flow channel 123, light emanating from light source 112 is alternately substantially transmitted to object 105 and substantially blocked or partially blocked from reaching object 105 as object 105 travels along flow direction 123c. The alternate transmission and non-transmission (or reduced transmission) of measurement light 112a along flow direction 123c produces time-varying light 107 emanating from object 105. Time-varying light 107 emanating from object 105 falls on detector 130 and, in response, detector 130 generates time-varying detector output signal 134.

According to some embodiments of assembly 100 that include the output spatial filter configuration, light 112a from light source 112 illuminates object 105, causing object 105 to emanate light 107. As object 105 travels in flow direction 123c in detection region 123b of flow channel 123, the output spatial filter alternatively entirely or substantially blocks light 107 emanating from object 105 from reaching detector 130 and substantially transmits light 107 emanating from object 105 to detector 130. The alternate substantial transmission and blocking (or partial blocking) of light 107 emanating from object 105 as object 105 flows through detection region 123b produces time varying light that falls on detector 130. In response, detector 130 generates time-varying detector output signal 134.

In some embodiments such as the embodiment of FIG. 1, assembly 100 may include signal processor 140 that converts time-varying detector output signal 134 to frequency domain output signal 136 so as to provide spectral power as a function of frequency. Signal processor 140 may be part of detector 130 in some embodiments or may comprise separate circuitry in other embodiments. For example, in some embodiments, signal processor 140 may be part of analyzer 150 circuitry along with the detector. For conversion, signal processor 140 may use known techniques such as discrete Fourier transform including, for example, a Fast Fourier Transform "FFT" algorithm. Thus, frequency domain output signal 136 represents the frequency component magnitude of time-varying detector output signal 134, where the frequency component magnitude is the amount of a given frequency component that is present in time-varying detector output signal 134 or function. The Fourier signal power is a relevant parameter or measure because it corresponds to the function or value one would obtain by calculating in a straightforward manner the Fourier transform (e.g. using a Fast Fourier Transform "FFT" algorithm) of time-varying output signal 134. However, other methods or techniques of representing the frequency component magnitude, or other measures of the frequency component magnitude, may also be used. Examples may include e.g., the square root of the Fourier signal power, or the signal strength (as measured in voltage or current) obtained from a filter that receives as input time-varying detector output signal 134.

In FIG. 1, time-varying detector output signal 134 and/or frequency domain detector output signal 136 can be passed to analyzer 150. Analyzer 150 is configured to receive time-varying detector output signal 134 and/or frequency domain detector output signal 136 and to determine characteristics of object 105 in one or more dimensions including at least a size based upon time-varying detector output signal 134 and/or frequency domain detector output signal 136. As will be discussed subsequently, the various embodiments discussed herein provide examples of techniques for determining the size of object 105 using various mask designs and processing techniques.

Figure 2:
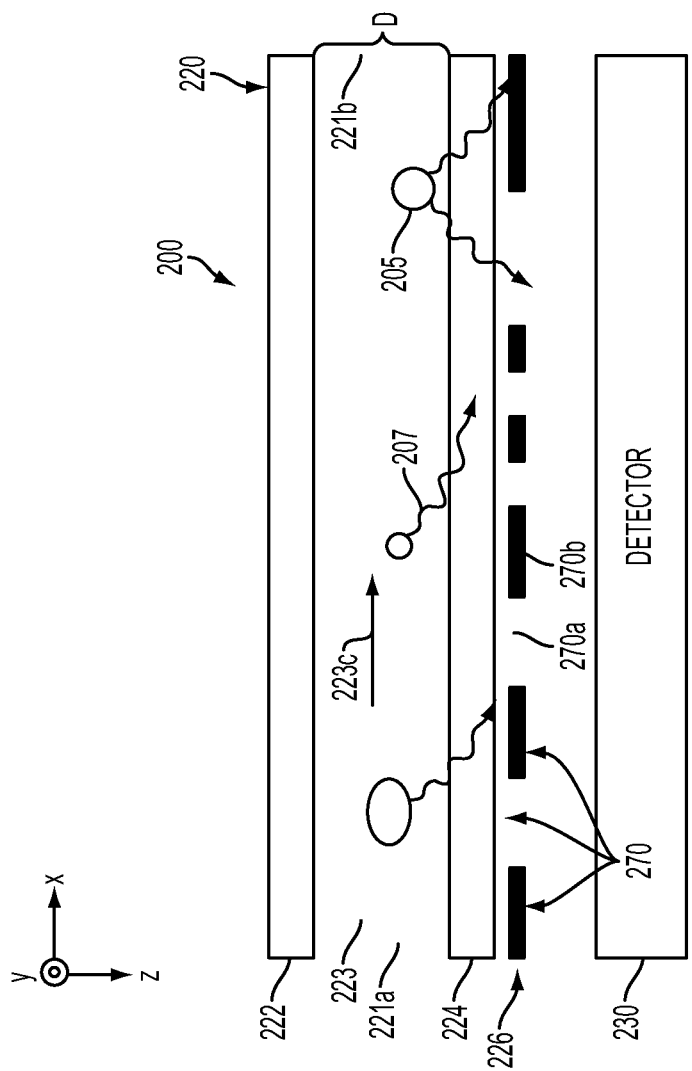
FIG. 2 is a schematic view of another example embodiment of an assembly with the spatial filter positioned between the object and the detector with the spatial filter spaced apart from the flow channel.

FIG. 2 is an enlarged schematic view of a portion of assembly 200 according to another example embodiment. The portion of assembly 200 illustrated in FIG. 2 includes a flow path, e.g., fluidic structure 220, detector 230, and spatial filter 226. Fluidic structure 220 is adapted to receive a sample of interest to be analyzed. The sample may enter the fluidic structure 220 at inlet 221a thereof, that can, in some embodiments, be a pipettor tip; and exit fluidic structure 220 at outlet 221b, flowing generally in flow direction 223c along the x-direction through flow channel 223 formed between confining members 222 and 224. As illustrated in FIG. 2, one or more objects 205 can be disposed at various locations within flow channel 223 and can have different sizes.

As discussed previously, spatial filter 226 may comprise, for example, a spatial mask. As will be discussed in greater detail subsequently, spatial filter 226 may have a plurality of mask features 270. Mask features 270 can include light transmissive regions 270a and less transmissive regions 270b. The pattern or sequence of transmissive regions 270a and less transmissive regions 270b define a transmission function that changes based on the size and shape of the object. This transmission function may be substantially periodic, or it may instead be substantially non-periodic. The transmission function is sensed by detector 230, which is configured to output the time-varying output signal discussed in FIG. 1 in response.

In the embodiment of FIG. 2, spatial filter 226 may be substantially monochromatic or polychromatic as desired. In a monochromatic mask, transmissive regions 270a all have substantially the same transmission characteristic across a certain spectral region, and non-transmissive regions 270b also all have substantially the same transmission characteristic across this spectral region (but different from that of transmissive regions 270a). In a simple case, transmissive regions 270a may all be completely clear, as in the case of an aperture, and less transmissive regions 270b may be completely opaque, as in the case of a layer of black ink or other absorptive, reflective, or scattering material. Alternatively, transmissive regions 270a may all have a given color or filter characteristic, e.g., high transmission for light emanating from an excited object, but low transmission for measurement light. Alternatively, less transmissive regions 270b may have a low but non-zero light transmission, as in the case of a grey ink or coating, or a partial absorber or reflector.

In the embodiment of FIG. 2, spatial filter 226 is positioned between objects 205 and detector 230. Light 207 emanating from objects 205 interacts with spatial filter 226 to provide modulation of the sensed light that falls on detector 230. In the illustrated embodiment, spatial filter 226 can be positioned between objects 205 and detector 230 and spatial filter 226 and detector 230 and can be spaced apart from flow channel 223 (and confining member 224).

Figure 3:
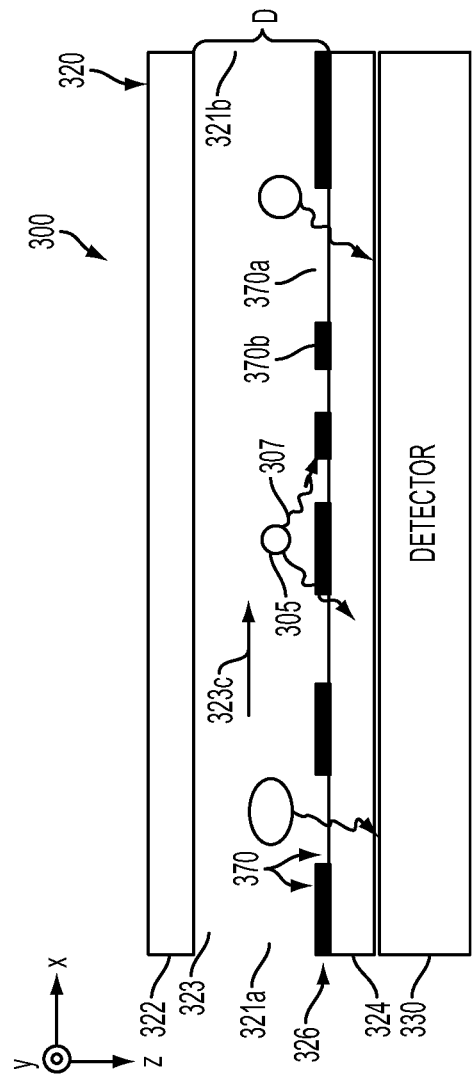
FIG. 3 is a schematic view of yet another example embodiment of an assembly with the spatial filter positioned between the object and the detector with the spatial filter positioned within the flow channel.
Figure 4:
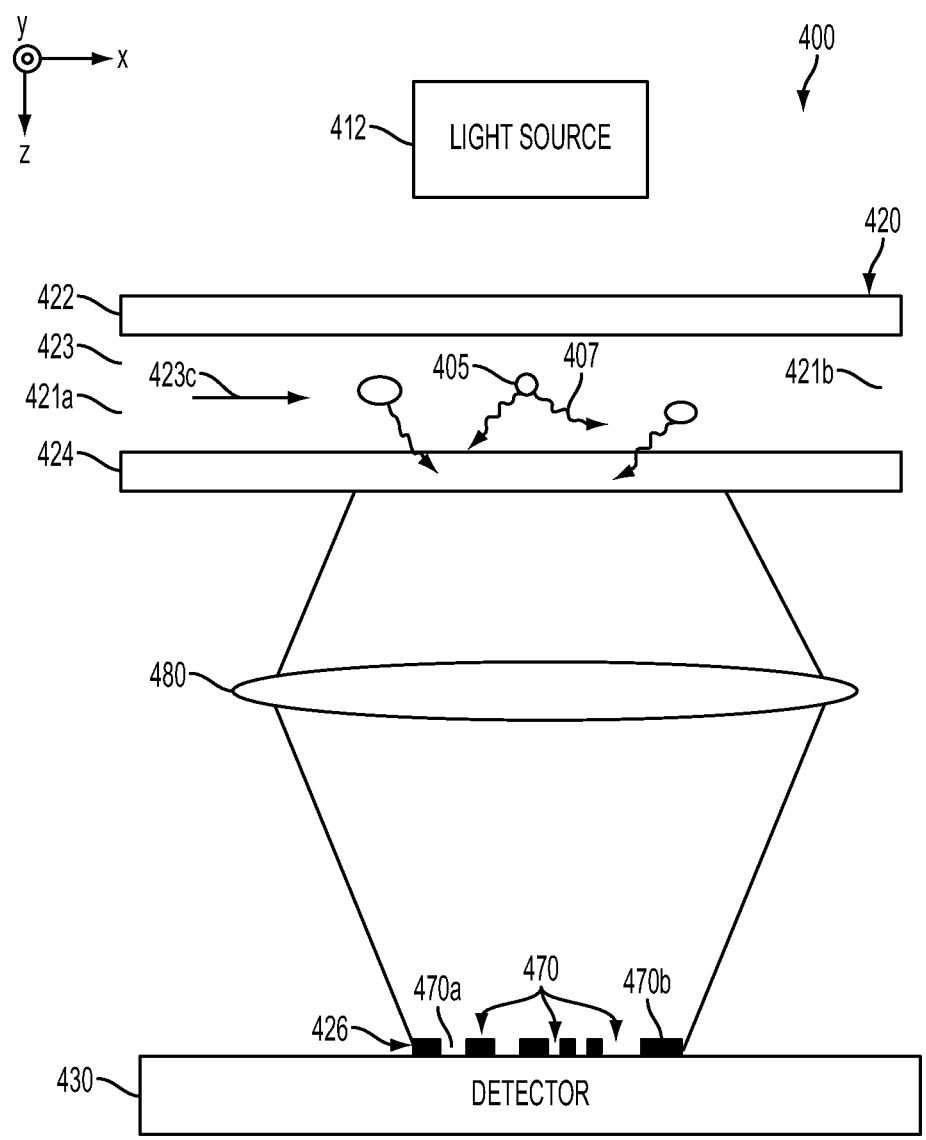
FIG. 4 is a schematic view of another example embodiment of an assembly with an optical imaging element positioned between the object and detector and the spatial filter positioned adjacent the detector.

FIG. 3 is an enlarged schematic view of a portion of assembly 300 according to another example embodiment. The portion of assembly 300 illustrated includes a flow path, e.g., fluidic structure 320, detector 330, and spatial filter 326. Similar to the embodiments of FIGS. 1 and 2A, structure 320 includes inlet 321a, outlet 321b, flow channel 323 having a flow direction 323c, and confining members 322 and 324. As illustrated in FIG. 2C, one or more objects 305 have different shapes and/or sizes in the x and z directions and are disposed within flow channel 323. Spatial filter 326 includes mask features 370 with light transmissive regions 370a and less transmissive regions 370b. In the embodiment of FIG. 3, spatial filter 326 is positioned between objects 305 and detector 330. However, spatial filter 326 is positioned proximate to or within flow channel 323. FIG. 4 is a schematic view of another embodiment of a portion of assembly 400 according to another example of remote sensing. The portion of assembly 400 illustrated includes light source 412, spatial filter 426, flow path, e.g., fluidic structure 420, and detector 430. Similar to the embodiments of FIGS. 1, 2, and 3, fluidic structure 420 includes inlet 421a, outlet 421b, flow channel 423 having flow direction 423c, and confining members 422 and 424. Spatial filter 426 includes mask features 470 with light transmissive regions 470a and less transmissive regions 470b. In FIG. 4, spatial filter 426 is positioned between objects 405 and detector 430 and is positioned remotely from flow channel 423 immediately adjacent detector 430. Optical imaging element 480 such as, for example, a lens, microlens array, or micromirror array, is positioned between objects 405 and filter 426 and is configured to image light from objects 405 onto at least one of spatial filter 426 and detector 430. The light emanating from objects 405 and imaged by element 480 interacts with spatial filter 426 to provide modulation of the sensed light received by detector 430.

Figure 5:
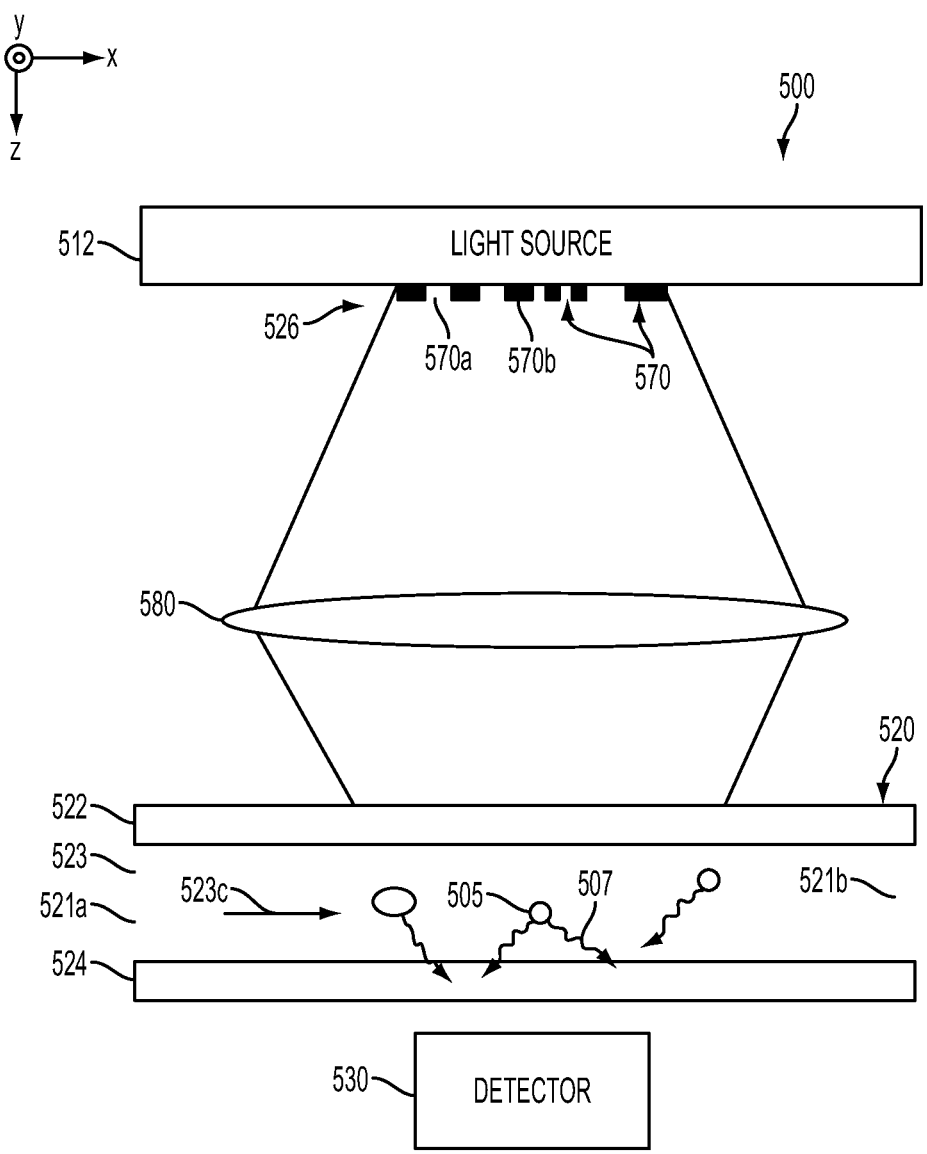
FIG. 5 is a schematic view of another example embodiment of an assembly with the optical imaging element positioned between the light source and the detector and the spatial filter positioned adjacent the light source.

FIG. 5 is a schematic view of yet another embodiment of a portion of assembly 500. The portion of assembly 500 illustrated includes light source 512, spatial filter 526, a flow path, e.g., fluidic structure 520, and detector 530. Similar to the previously discussed embodiments, fluidic structure 520 includes inlet 521a, outlet 521b, flow channel 523 having flow direction 523c, and confining members 522 and 524. Spatial filter 526 includes mask features 570 with light transmissive regions 570a and less transmissive regions 570b. In FIG. 5, spatial filter 526 is positioned between light source 512 and fluidic structure 520 containing objects 505. As shown, spatial filter 526 is positioned remotely from flow channel 523 immediately adjacent light source 512. Interaction between the output light from light source 512 and spatial filter 526 causes spatially modulated measurement light 512a. Optical imaging element 580 is positioned between filter 526 and objects 505 and is configured to image spatially modulated measurement light 512a onto a measurement region of flow channel 523. Additionally, optical imaging element 580 may incorporate one or more filters to narrow or otherwise tailor the spectrum of the resultant spatially modulated measurement light. The spatially modulated measurement light causes light 507 emanating from objects 505 to be spatially modulated as well. The spatially modulated light emanating from objects 505 sensed by the detector 530.

Figure 6:
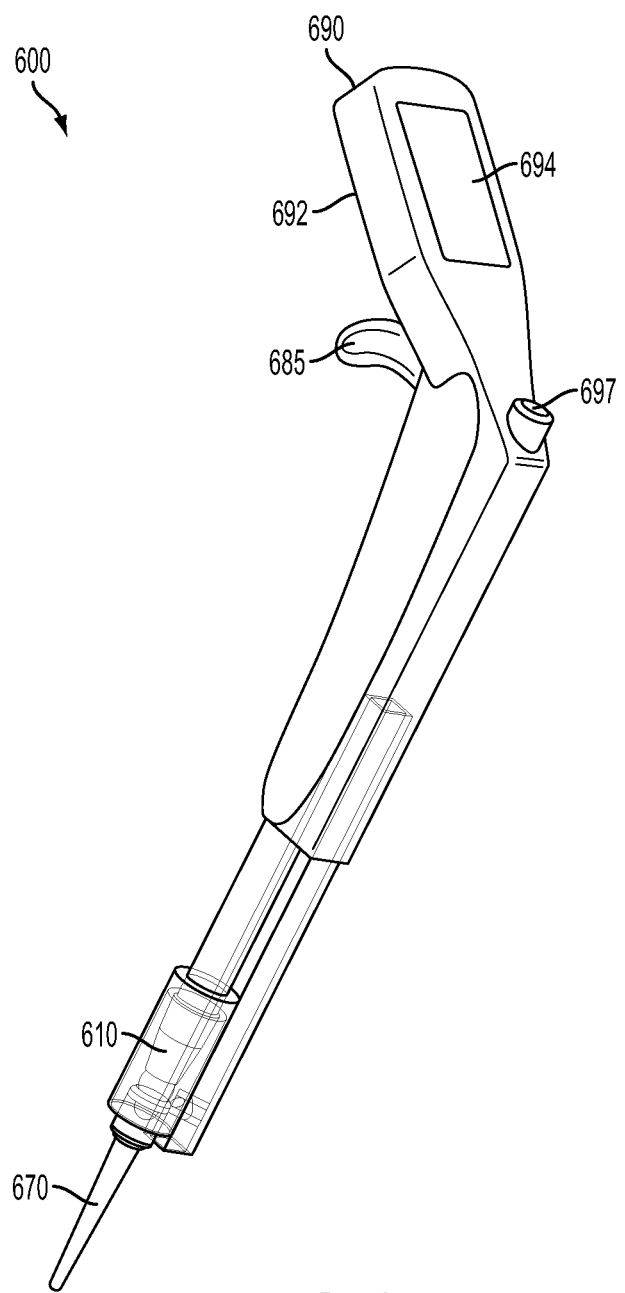
FIG. 6 is a perspective view of an example embodiment of a flow cytometer that includes a fluidic optical cartridge engaged in a host structure.

FIG. 6 is a perspective view of an example embodiment of a flow cytometer that includes a fluidic optical cartridge engaged in a host structure. Flow cytometer 600 can be a point-of-use device and can be hand-held. In this disclosure, hand-held indicates that in normal use the disclosed flow cytometer is portable, self-contained, and small enough to be operated manually, although it is recognized that it is possible to operate it using, for example, robotics. One property of the disclosed flow cytometer is that it can be physically moved to the sample rather than having the sample brought and loaded into the cytometer. In the embodiment illustrated in FIG. 6, flow cytometer 600 includes handle 685 for ease of manual use. In some embodiments the disclosed flow cytometer is that it is physically small enough to be held in the operator's hand. In some embodiments, the weight of the disclosed flow cytometer can be 1 kg or less, 0.75 kg or less, or even 0.5 kg or less. Additionally, or alternatively, the volume of the disclosed flow cytometer that is a component of the disclosed flow cytometer can be 2 L or less, or 1 L or less. In this disclosure the volume does not refer to the liquid handling capacity of the fluidic structure but rather the volume of water the device would displace if it were submerged therein.

Cytometer 600 includes fluidic optical cartridge 610 that is engaged in pipettor tip 670. Pipettor tip 670 can be any pipettor tip that is useful in existing manual or pipettors. In some embodiments, pipettor tip 670 can be one or more of multichannel pipettor tips. Such multi-channel pipette tips are available, for example, from many of the sources listed below and also from Sartorius, Bohemia, N.Y. under the tradename BIOHIT PROLINE, BIOHIT m-LINE, or BIOHIT e-line. The disclosed apparatus or a plurality of disclosed apparatuses can also be adapted to robotic liquid handling systems such as, for example, those available under the tradename EVO by the Tecan Systems, Inc., San Jose, Calif.

Fluidic optical cartridge 610 is at least partially engaged in compartment 691 of host structure 690. Host structure 690 includes features, some of which are illustrated in FIG. 6. Host structure 690 includes a head part that can include electronics 692 that can process and/or analyze one or more electrical signals from a detector (also present in the host structure but not visible in FIG. 6. The head part of host structure 690 also can include display 694 and/or controls (not shown) for operation of flow cytometer 600. Electronics 692 can include an analyzer configured to analyze the electrical signals from the detector to identify characteristics of the objects. Additionally electronics 692 can, in some embodiments, be configured to output data information about these analyses, the information sometimes referred to herein as "data," over a wired or wireless network. Illustrated hand-held flow cytometer 600 can be completely self-contained and can include a power source as part of its electronics 692. It is capable of processing signals from its detector and of displaying the processed data in display 694. Alternatively, data can be sent to an external analyzer and analyzed at a remote location.

FIG. 6 also show button 697 which is in mechanical or electromechanical communication with a button shaft shown more clearly in FIGS. 12A, 14, and 16A-C). As will be discussed further on, button 697 can operate in three different positions that can put cytometer 600 in a "ready" mode, a "measure" mode, and an "eject" mode. The button shaft can move the path of measurement light emitted by the waveguide into position to deliver light to the fluidic optical cartridge and, in another movement, can eject the whole fluidic optical cartridge which can be a disposable unit.

Figure 7A:
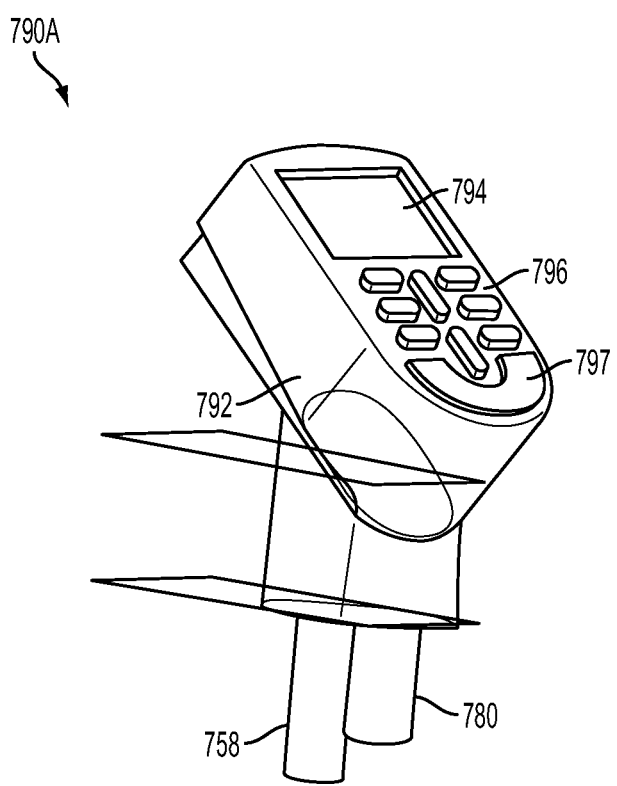
FIGS. 7A and 7B are two perspective views of a head portion of an example embodiment of a disclosed host structure.
Figure 7B:
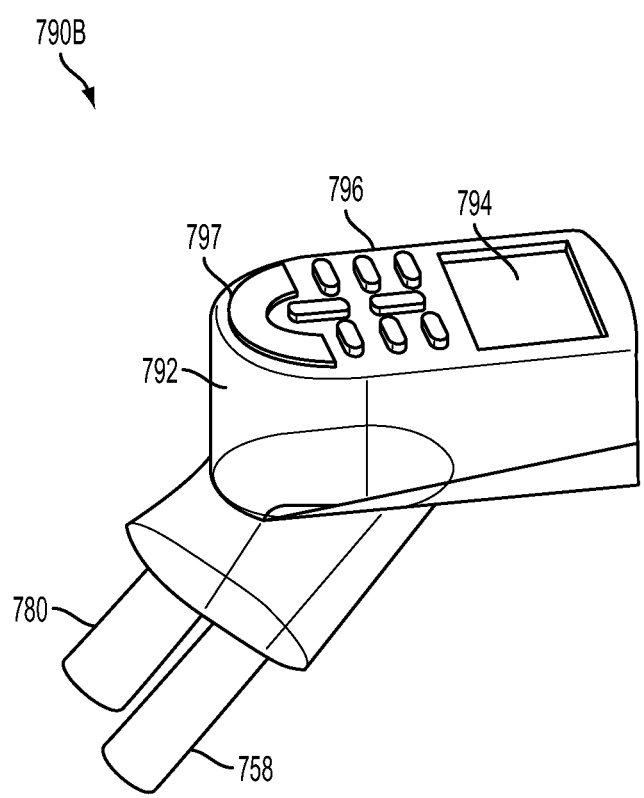

FIGS. 7A and 7B are two perspective views 790A and 790B of a head portion of an example embodiment of a disclosed host structure. The illustrated head portions include display 794, controls 796 and button 797 as also shown in FIG. 6. The portion of the head portion of the illustrated host structure also includes waveguide 758 configured to deliver measurement light to a compartment at least partially within the host structure. When a fluidic optical cartridge is engaged in the compartment, waveguide 758 is configured to deliver measurement light to a transparent optical region of the fluidic optical cartridge containing objects in an analyte fluid. Waveguide 758 can be any feature that can conduct measurement light from a light source to the compartment of the host structure. In some embodiments, the light source can be a laser diode or semiconductor laser that is located in the head of the host structure. Waveguide 750 can be any optical conductor and can include slab waveguides, optical fibers, polymer rods, polymer fibers, and any other optical conductors that are transparent to the wavelength of the light source. Free space light guiding may also be used for parts of the complete optical path. In some embodiments, waveguide 750 can be a hollow tube (cylindrical or otherwise shaped) having at least one mirror at the end that can guide light from the light source into the compartment of the host structure. In other embodiments, waveguide 750 can be a portion of a hollow cylinder such as a 90 degree section of a cylinder.

Figure 8:
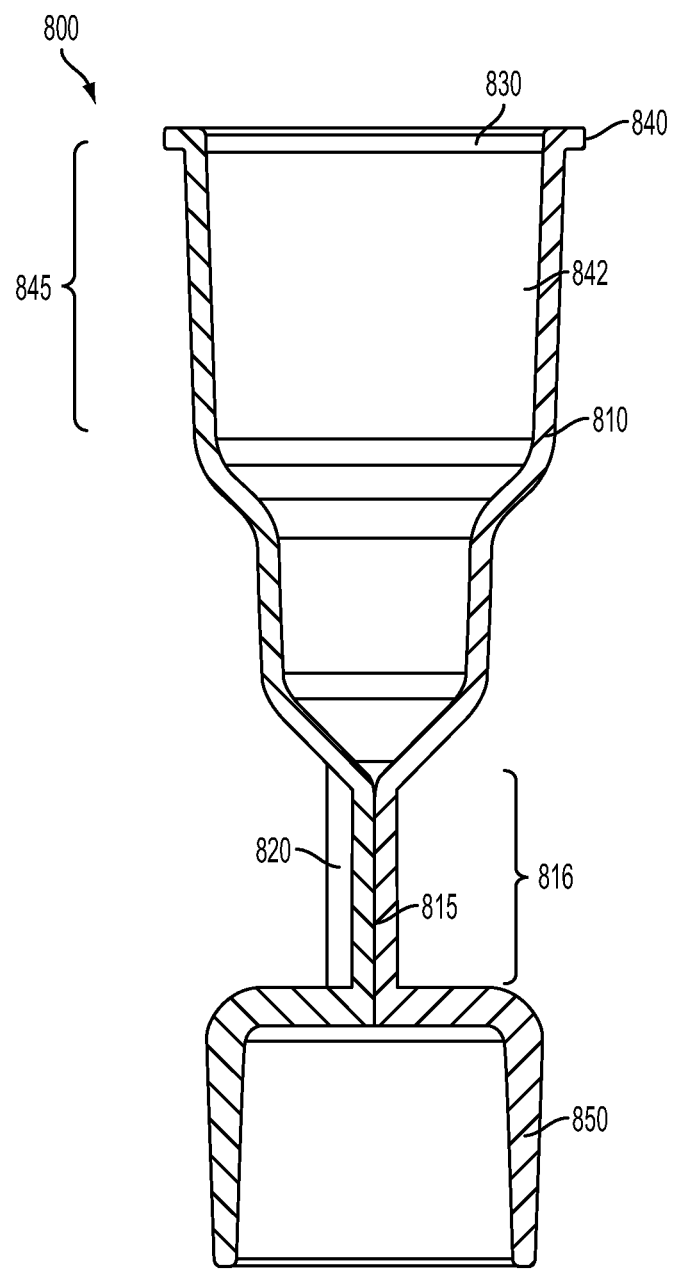
FIG. 8 is a side cut-away view of a fluidic optical cartridge useful in an example embodiment of a disclosed host structure.

FIG. 8 is a side cut-away view of a fluidic optical cartridge useful in an example embodiment of a disclosed host structure. FIG. 8 is a side cutaway view of an apparatus according to an example embodiment. Fluidic optical cartridge 800 includes fluidic structure 810. Fluidic structure 810 includes transparent channel 815 through which objects in a fluid can travel along respective paths during operation of fluidic optical cartridge 800. Fluidic optical cartridge 800 also includes optical component 820 (partially behind transparent channel 815 in FIG. 8 but visible in FIG. 9). Optical component 820 can include a light-redirecting element. In the embodiment shown in FIG. 8, the light-redirecting element can be a lens element that can redirect measurement light from an outside source (host structure) to the objects traveling through transparent channel 815. In the embodiment shown in FIG. 8, the light-redirecting element is a lens element that can redirect measurement light from an outside source (host structure) to the objects traveling through the transparent channel within transparent optical region 816.

Fluidic optical cartridge 800 can be made of transparent polymeric material such as, for example, poly(methyl methacrylate), polypropylene, polycarbonate, or polyethylene. In some embodiments at least one wall of transparent optical region 816 need be transparent and the remainder of fluidic optical cartridge can be made of other materials.

Fluidic optical cartridge 810 can be reversibly engaged with a host structure. The host structure (not shown) can include a light source, a waveguide to deliver light to transparent channel 815, and an air piston configured to provide air (or vacuum) to fluidic optical cartridge 800 to control fluid movement into and out of fluidic optical cartridge 800. Accordingly, fluidic optical cartridge 800 includes flange 840 that is configured to reversibly engage with a host structure. In FIG. 8, taper 842 is configured to fit into a male taper in the host structure to form a seal. In some embodiments, the male taper of the host structure can be part of a button shaft that includes an air cylinder therewithin and can fit snugly into taper 842 and can make an air-tight seal with fluidic optical cartridge 800. The seal can be snug enough to allow air or vacuum to control fluid movement into and out of apparatus 800.

Fluidic optical cartridge 800 also includes mating end 850 (pictured in FIG. 8 as a tapered female socket, but not limited to that feature) that is configured to engage a pipettor tip. Typical pipettor tips have various mating features such as, for example, repositionable tip fitting mounting shafts, coupling elements, mounting segments, or tapers. Mating end 850 can be designed to fit any disposable pipettor tips and can have appropriate button shaft stopping features and, if present in the pipettor tip, interlocking features such as an interlock tab. Mating end 850 can be configured to fit repositionable pipettor tips made by Rainin Instrument, LLC., (Oakland, Calif.), Eppendorf AG, Hamburg, GERMANY, Quigen GmbH, Hilden, GERMANY, Thermo-Fisher (Minneapolis, Minn.), Hoffman La Roche (Basel, Switzerland), Gilson (Middleton, Wis.), Hamilton Company (Reno, Nev.), and Viaflow Corporation, Hudson, N.H. It is also contemplated that the disclosed apparatus can be adapted to and utilized with multi-channel pipettor tips (pipettes). Such multi-channel pipette tips are available, for example, from many of the sources listed above and also from Sartorius, Bohemia, N.Y. under the tradename BIOHIT PROLINE, BIOHIT m-LINE, or BIOHIT e-line. The disclosed apparatus or a plurality of disclosed apparatuses can also be adapted to robotic liquid handling systems such as, for example, those available under the tradename EVO by the Tecan Systems, Inc., San Jose, Calif.

Figure 9:
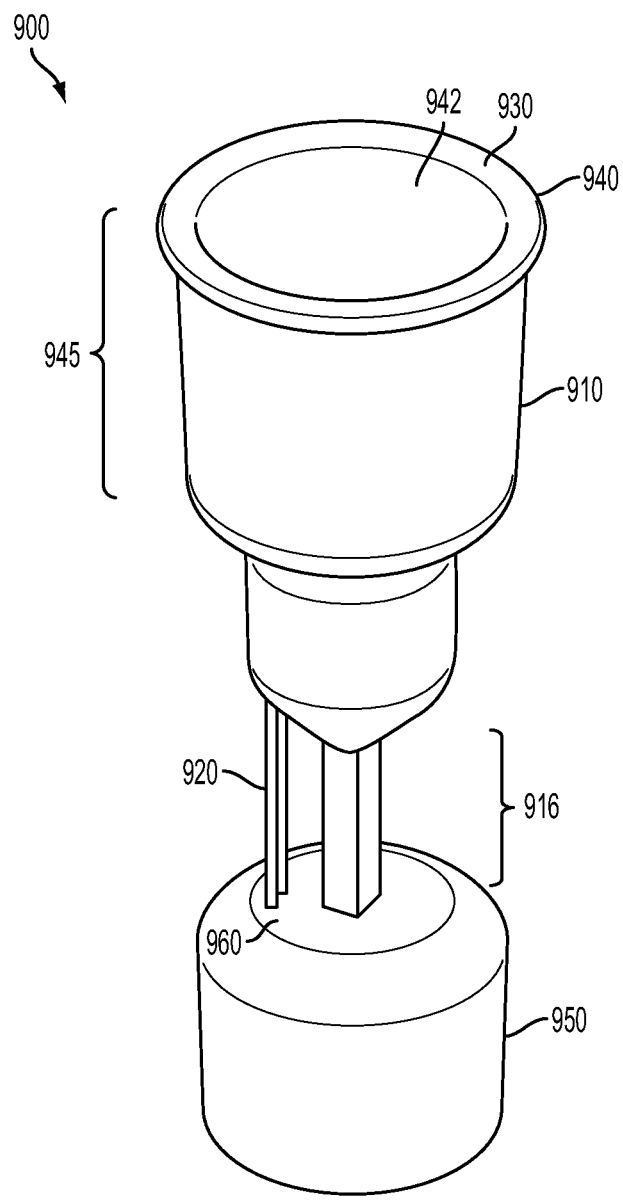
FIG. 9 is a perspective view of the apparatus shown in FIG. 8.

FIG. 9 is a perspective view of the apparatus illustrated in FIG. 8 showing some of the features more clearly. Optical fluidic cartridge 900 includes fluidic structure 910. Fluidic structure 910 includes transparent optical region 916 concealing a channel (not visible in FIG. 9) through which objects in a fluid can travel along respective paths during operation of fluidic optical cartridge 900. Fluidic optical cartridge 900 also includes optical component 920. Optical component 920 can include a light-redirecting element. In the embodiment shown in FIG. 9, the light-redirecting element is a lens element that can redirect measurement light from an outside source (host structure) to the objects traveling through the transparent channel within transparent optical region 916.

Fluidic optical cartridge 900 can be reversibly engaged with a host structure. The host structure (not shown) can include a light source, a waveguide to deliver light to the transparent channel in transparent optical region 916, and an air piston configured to provide air (or vacuum) to fluidic optical cartridge 900 to control fluid movement into and out of fluidic optical cartridge 900. Accordingly, fluidic optical cartridge 900 includes flange 940 that is configured to reversibly engage with a host structure. In FIG. 9 taper 942 is configured to fit into a male taper in the host structure.

Fluidic optical cartridge 900 also includes mating end 950 that is configured to engage a pipette tip, typically a pipettor tip. Typical pipettor tips have various mating features such as, for example, repositionable tip fitting mounting shafts, coupling elements, mounting segments, or tapers. Mating end 950 can be designed to fit any disposable pipettor tips and can have appropriate air-sealing features and, if present in the pipettor tip, interlocking features that complement the pipettor tip. Mating end 950 can be configured to fit repositionable pipettor tips made by Rainin Instrument, LLC (Oakland, Calif.), Eppendorf AG, Hamburg, GERMANY, Quigen GmbH, Hilden, GERMANY, Thermo-Fisher (Minneapolis, Minn.), Hoffman La Roche (Basel, Switzerland), Gilson (Middleton, Wis.), Hamilton Company (Reno, Nev.), and Viaflow Corporation, Hudson, N.H. It is also contemplated that the disclosed apparatus can be adapted to and utilized with multi-channel or single-channel pipettors (pipettes). Such multi-channel pipettors are available, for example, from many of the sources listed above and also from Sartorius, Bohemia, N.Y. under the tradename BIOHIT PROLINE, BIOHIT m-LINE, or BIOHIT e-line. The disclosed apparatus or a plurality of disclosed apparatuses can also be adapted to robotic liquid handling systems such as, for example, those available under the tradename EVO by the Tecan Systems, Inc., San Jose, Calif. or other automated devices.

Both transparent fluidic optical region 916 and optical component 920 are fixed to base plate 960 so that they maintain fixed positions with respect to each other. The optical component and the transparent optical region are in a fixed spatial relationship with each other facilitating the use of the cartridge in the host structure since important optical alignments in the cartridge are molded into the piece. In some embodiments, the fluidic structure and the optical component can be molded as one piece. Any other permanent alignment may also serve the same purpose.

Figure 10A:
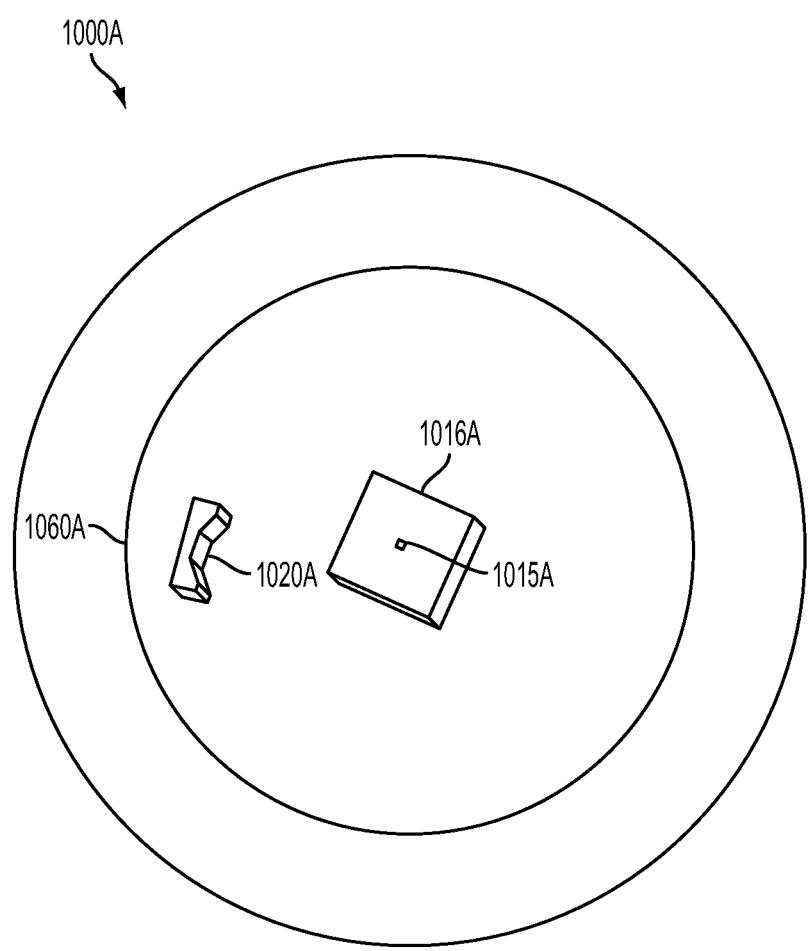
FIGS. 10A-10D are cut-away top down views of various example embodiments of a fluidic optical cartridges useful in a disclosed host structure.

FIGS. 10A-10D are cut-away top down views of various example embodiments of a fluidic optical cartridges useful in a disclosed host structure. FIG. 10A is a top down view of base plate 960 shown in FIG. 9. Base plate 1060A is connected to transparent optical region 1016A (cross-section shown in FIG. 10A that also is an illustration of transparent fluidic channel 1015A) and optical component 1020A. In the embodiment illustrated in FIG. 10A, optical component 1020A is shown as a concave reflecting mirror (light redirecting element), but, as mentioned above, any other optical component that modifies the measurement light and delivers the modified light through fluidic optical region 1016A into transparent fluidic channel 1015A. For example, optical component 1020A can be any combination of, but not limited to, lenses, mirrors, prisms, gratings, phase retardation plates or optical modulation devices. Optical component 1020A is at a fixed position to transparent fluidic optical region 1016A (and transparent fluidic channel 1015A). The critical optical alignments are physically locked into position by in the disclosed apparatus. In the example embodiment illustrate in FIG. 10A, there is one optical component 1020A and one transparent optical region 1016A. The optical component can be a mirror (a concave mirror is shown in FIG. 10A).

Figure 10B:
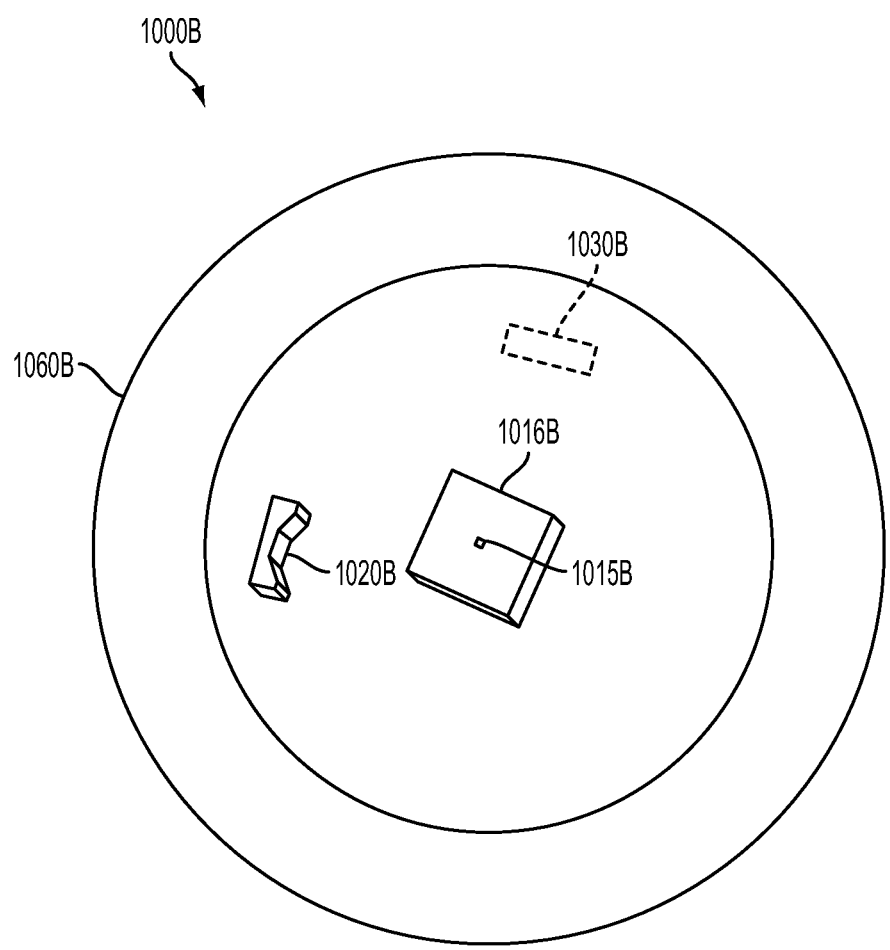
Figure 10C:
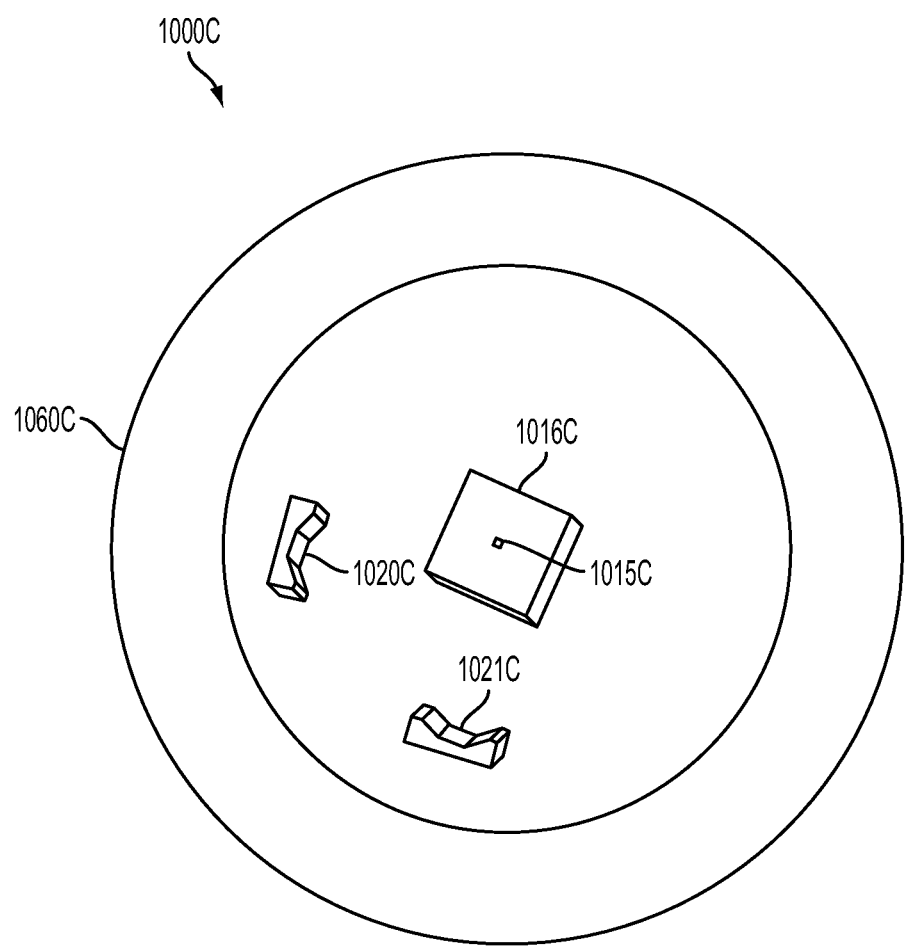

FIG. 10B is an illustration of another example embodiment of a disclosed apparatus. Base plate 1060B is connected to transparent optical region 1016B (cross-section shown in FIG. 10B that also is an illustration of transparent fluidic channel 1015B) and optical component 1020B. In the embodiment illustrated in FIG. 10B, optical component 1020B is shown as a concave reflecting mirror (light-redirecting element), but, as mentioned above, any other optical component that modifies the measurement light and delivers the modified light through transparent optical region 1016B into fluidic channel 1015B. Fluidic optical cartridge 1000B in FIG. 10B also includes filter assembly 1030B that can take output light emanating from the objects travelling in the channel and modify it before it reaches detectors in the host structure. In some embodiments, the filter assembly can be a mask that is directly in contact with transparent optical region 816B. Filter assembly 1030B can be located on base plate 1060B and can include encoding components, decoding components, imaging components, spatial filters, masks, and a combination of these features. In some embodiments, the encoding components and/or decoding components can be color filters. FIG. 10C is an illustration of another example embodiment of a disclosed fluidic optical cartridge. Base plate 1060C is connected to transparent optical region 1016C (cross-section shown in FIG. 10C that also is an illustration of transparent fluidic channel 1015C) and optical components 1020C and 1021C. In the embodiment illustrated in FIG. 10C, optical components 1020C and 1021C are shown as a concave reflecting mirrors (light-redirecting elements), but, as mentioned above, any other optical component that modifies the measurement light and delivers the modified light through transparent optical region 1016C into fluidic channel 1015C. Fluidic optical cartridge 1000C in FIG. 10C can be used, for example, in a host structure that includes two sources of measurement light that can be, for example, at two different wavelengths, two different phases, two different modulations, etc.

Figure 10D:
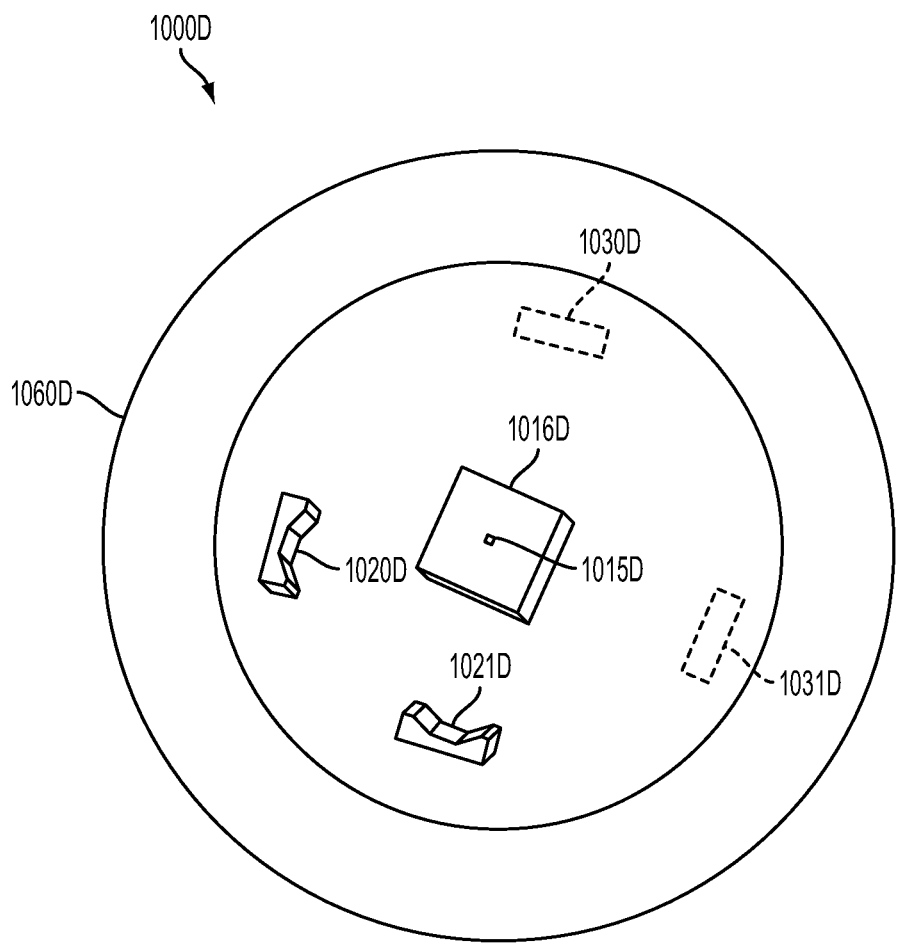

FIG. 10D is an illustration of another example embodiment of a disclosed fluidic optical cartridge that may also be present in a disclosed apparatus. Base plate 1060D is connected to transparent fluidic optical region 1016D (cross-section shown in FIG. 10D that also is an illustration of transparent fluidic channel 1015D and optical components 1020D and 1021D). In the embodiment illustrated in FIG. 10D, optical components 1020D and 1021D are shown as a concave reflecting mirrors (light-redirecting elements), but, as mentioned above, any other optical component that modifies the measurement light and delivers the modified light through transparent optical region 1016D into fluidic channel 1015D. Fluidic optical cartridge 1000D in FIG. 10D also includes filter assemblies 1030D and 1031D. These filter assemblies may take output light emanating from the objects travelling in the channel and modify it before it reaches detectors in the host structure. Filter assemblies 1030D and 1031D can, optionally, be located on base plate 1060D.

Figure 11A:
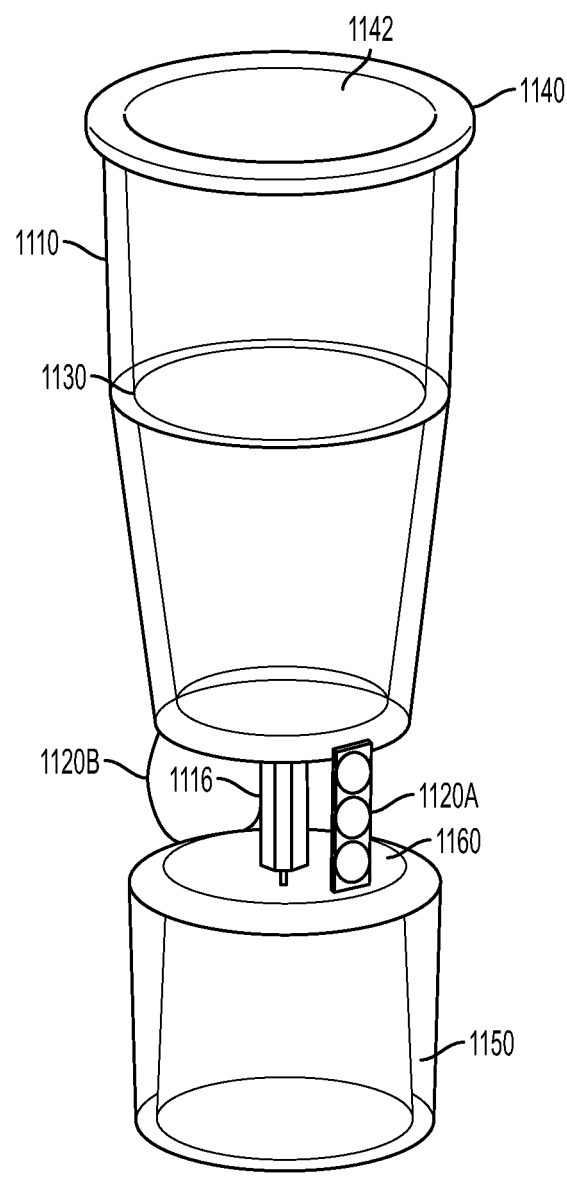
FIG. 11A is a side cross-sectional view of an example embodiment of a fluidic optical cartridges useful in a disclosed host structure.
Figure 11B:
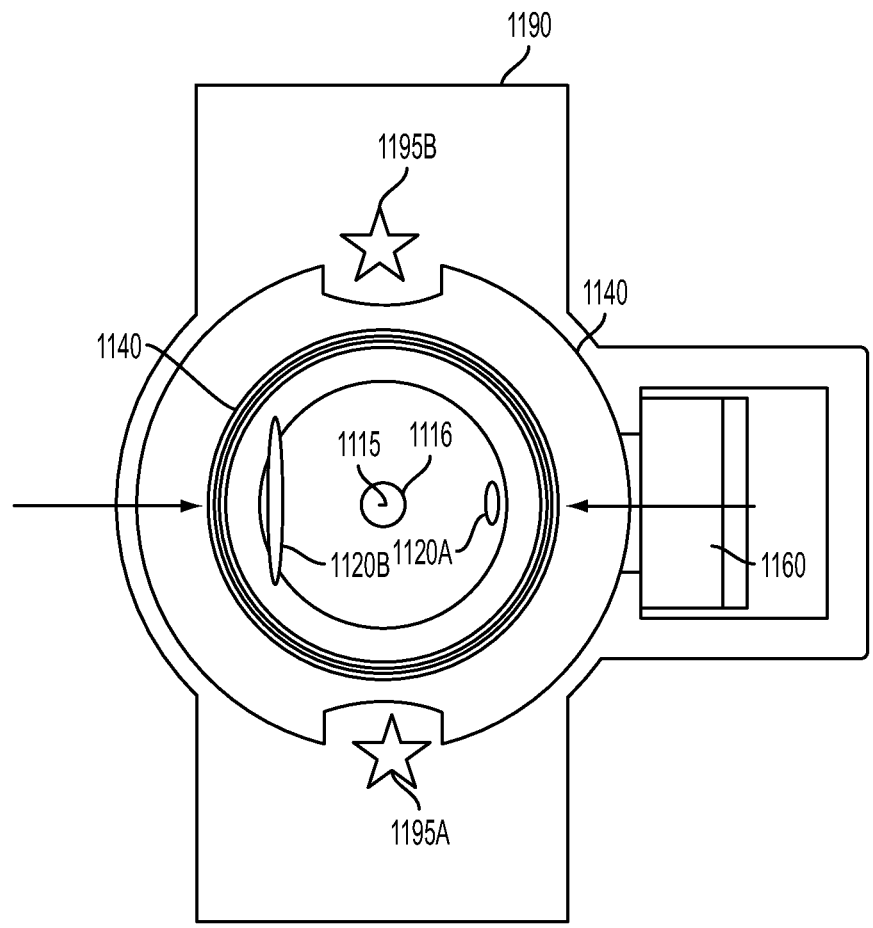
FIG. 11B is a top cross-sectional view of the same example embodiment shown in FIG. 11A.

FIGS. 11A and 11B are views of an example embodiment of a disclosed apparatus. FIG. 11A is a side perspective view of an example embodiment of a disclosed apparatus. FIG. 11B is a top cross-sectional view of the same example embodiment shown in FIG. 11A. FIG. 11A is an illustration of an embodiment of disclosed apparatus (fluidic optical cartridge) 1110. Apparatus 1110 includes transparent optical region 1116 concealing transparent channel 1115 (not visible in FIG. 11A) through which objects in a fluid can travel along respective paths during operation of apparatus 1110. Fluidic optical cartridge 1110 also includes two optical components 1120A and 1120B. In embodied fluidic optical cartridge 1110, optical component 1120A is shown as a microarray of lenses and optical component 1120B is shown as a single lens element. Illustrated fluidic optical cartridge 1110 is not limited to these specific components. Optical components 1120A and 1120B can be any light-redirecting element as discussed above. In some embodiments, the light-redirecting element can include a lens, a lens array, a microlens array, a mirror, or a micromirror array, or a combination thereof. In the embodiment shown in FIG. 11A, the light-redirecting elements can redirect measurement light from an outside source, such as a host structure, to create focus spots within transparent channel 1115. Apparatus 1110 has two optical components 1120A and 1120B for each of two beams of measurement light indicated by the two arrows (shown in FIG. 1120B).

Fluidic optical cartridge 1110 can be reversibly engaged with a host structure. The host structure (not shown in FIG. 11A but shown as 1190 in FIG. 11B) can include a light source, a waveguide to deliver light to transparent channel 1115 in transparent region 1116 as shown. In the example embodiment, the host structure includes two waveguides that emanate two beams of measurement light (shown by arrows in FIG. 11B). Fluidic optical cartridge 1110 includes flange 1140 that is configured to reversibly engage with host structure 1190. Fluidic optical cartridge 1110 also includes button shaft stop 1130 that can act as a stop when fluidic optical cartridge 1110 is engaged with a projecting male tapered part of host structure 1190. In some embodiments, the projecting male tapered part of the host structure can fit snugly into taper 1142 and can make a seal with fluidic optical cartridge 1110.

Fluidic optical cartridge 1110 also includes mating end 1150 that is configured to engage a pipettor tip. Both transparent optical region 1116 (that has transparent channel 1115 therewithin) and optical components 1120A and 1120B are fixed to base plate 1160. The optical components and the transparent optical region are in a fixed relationship with each other facilitating the use of the cartridge in the host structure since important optical alignments in the cartridge are molded into the piece. The two beams of measurement light (arrows in FIG. 11B) in host structure 1190 are opposite each other and impinge upon optical components 1120A and 1120B respectively. Also shown in FIG. 11B are two detectors 1195A and 1195B that, in the illustrated embodiment are at 90 degrees to the two beams of measurement light and can measure, for example, fluorescent or scattering emanations from objects traveling in the transparent channel within transparent optical region 1116.

Figure 12A:
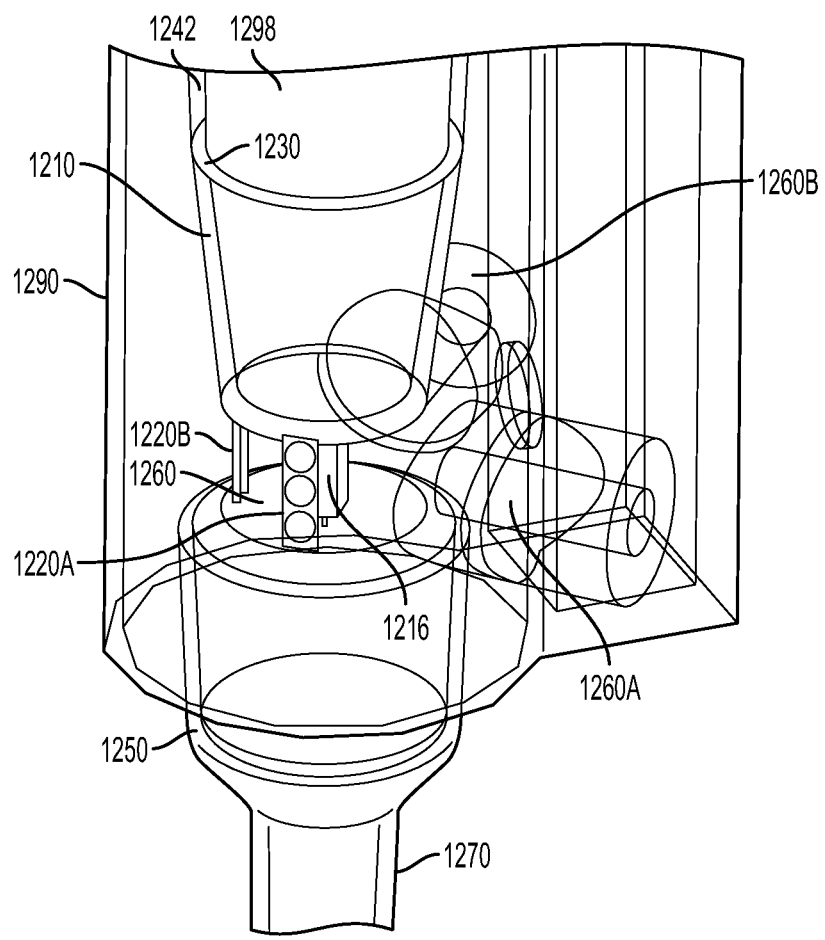
FIG. 12A is a side cross-sectional view of another example embodiment of a fluidic optical cartridges useful in a disclosed host structure.
Figure 12B:
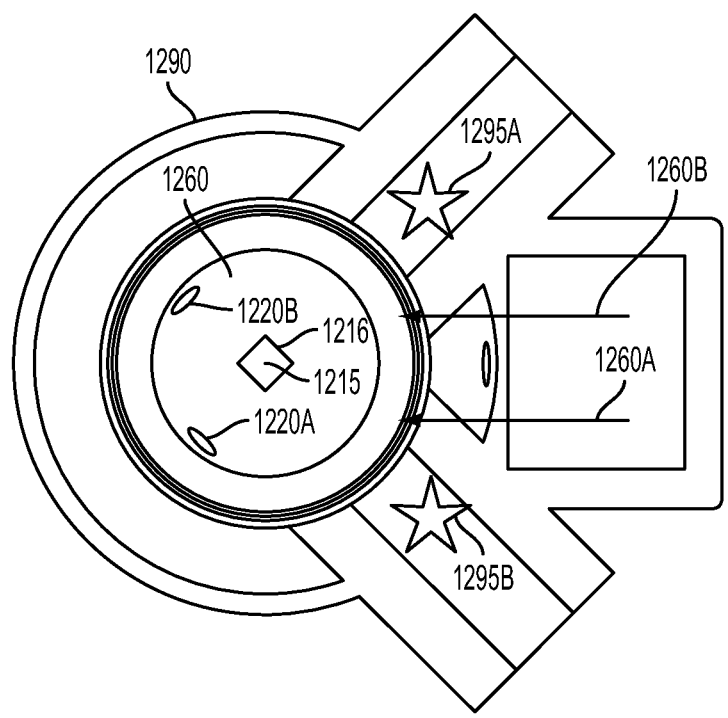
FIG. 12B is a top cross-sectional view of the same example embodiment shown in FIG. 12A.

FIGS. 12A and 12B are cutaway views of an example embodiment of a disclosed apparatus. FIG. 12A is a side cross-sectional view of an example embodiment of a disclosed apparatus. FIG. 12B is a top cross-sectional view of the same example embodiment shown in FIG. 12A. FIG. 12A is an illustration of an embodiment of disclosed apparatus (fluidic optical cartridge) 1210 inside host structure 1290 (partially cut away). Fluidic optical cartridge 1210 includes transparent optical region 1216 concealing transparent channel 1215 (not visible in FIG. 12A) through which objects in a fluid can travel along respective paths during operation of fluidic optical cartridge 1210. Fluidic optical cartridge 1210 also includes two optical components 1220A and 1220B. In illustrated and embodied fluidic optical cartridge 1210, optical components 1220A and 1220B are shown as microarrays of lenses. Illustrated fluidic optical cartridge 1210 is not limited to these specific components. Optical components 1220A and 1220B may be any light-redirecting element as discussed above. In the embodiment shown in FIG. 12A, the light-redirecting elements can redirect measurement light from an outside source (host structure) to the objects traveling through transparent channel 1215 within transparent optical region 1216. Fluidic optical cartridge 1210 has two optical components 1220A and 1220B for each of two beams of measurement light indicated by the two arrows (shown in FIG. 12B).

Fluidic optical cartridge 1210 can be reversibly engaged with a host structure. Host structure 1290 can include a light source, a waveguide to deliver light to the transparent channel in transparent optical region 1216 as shown. In the example embodiment, the host structure includes two waveguides that emanate two beams of measurement light (shown by arrows in FIG. 12B). Fluidic optical cartridge 1210 is configured to reversibly engage with host structure 1290. Fluidic optical cartridge 1210 also includes button shaft stop 1230. In some embodiments, a button shaft 1280 of host structure 1290 can fit snugly into taper 1242 and can make a seal with taper 1242 or at button shaft stop 1230.

Fluidic optical cartridge 1210 also includes mating end 1250 that is configured to engage pipettor tip 1270. Both transparent optical region 1216 (that has transparent channel 1215 therewithin) and optical components 1220A and 1220B are fixed to base plate 1260. The optical components and the transparent optical region are in a fixed relationship with each other facilitating the use of the cartridge in the host structure since important optical alignments in the cartridge are molded into the piece. The two beams of measurement light (arrows in FIG. 12B) in host structure 1290 are opposite each other and impinge upon optical components 1220A and 1220B respectively. In some embodiment, light can be reflected, either through a reflective surface that is printed, stamped, or deposited on fluidic optical cartridge 1210 or through a light guide (not shown) to the measurement area (transparent channel 1215). Alternatively, Also shown in FIG. 12B are two detectors 1295A and 1295B that, in the illustrated embodiment are at 45 degrees to the two beams of measurement light and can measure, for example, scattering emanations from objects traveling in the transparent channel within transparent optical region 1216.

Figure 13:
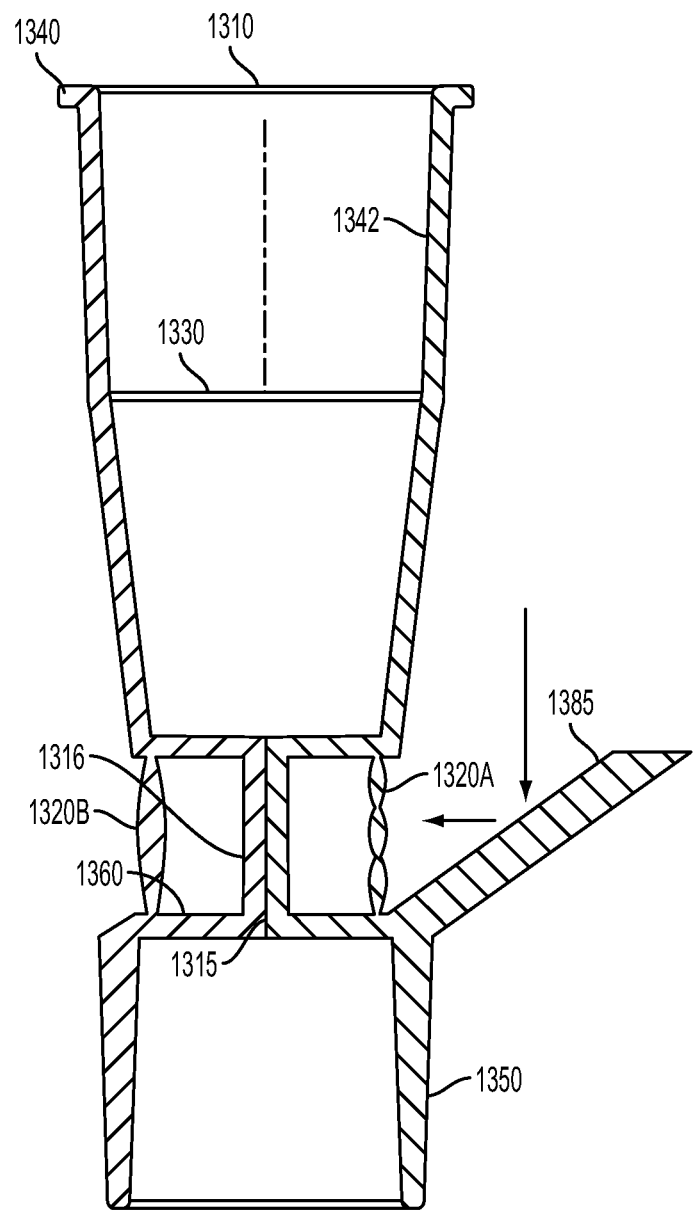
FIG. 13 is a side cutaway view of another fluidic optical cartridge useful in a disclosed host structure.

FIG. 13 is a side cutaway view of another example embodiment of a disclosed apparatus (fluidic optical cartridge). Fluidic optical cartridge 1310 includes transparent optical region 1316 having transparent channel 1315 therewithin through which objects in a fluid can travel along respective paths during operation of fluidic optical cartridge 1310. Fluidic optical cartridge 1310 also includes two optical components 1320A and 1320B. In embodied fluidic optical cartridge 1310, optical component 1320A is shown as a microarray of lenses and optical component 1320B is shown as a single lens element. Illustrated fluidic optical cartridge 1310 is not limited to these specific components. Optical components 1320A and 1320B can be any light-redirecting element as discussed above. In the embodiment shown in FIG. 13, the light-redirecting elements can redirect measurement light from an outside source (host structure) to the objects traveling through transparent channel 1315 within transparent optical region 1316. Fluidic optical cartridge 1310 also includes light-redirecting element 1385 that can redirect light (see arrows) from the host structure so that it impinges upon optical component 1320A (or 1320B) which can then focus light on objects traveling in transparent channel 1315. Light-redirecting element 1385 can be a mirror, lens, lens array, waveguide, or any other light-redirecting element and can be integrated into fluidic optical cartridge 1310. This can eliminate the need for the measurement light to be reflected by the host structure. In some embodiments, there can be more than one light redirecting element.

Fluidic optical cartridge 1310 can be reversibly engaged with a host structure. The host structure (not shown in FIG. 13 can include a light source, a waveguide to deliver light to the light-redirecting element 1385 which then delivers light to transparent channel 3115 within which objects in a fluid travel. Fluidic optical cartridge 1310 includes flange 1340 that is configured to reversibly engage with the host structure. Fluidic optical cartridge 1310 also includes button shaft stop 1330 that can seal when apparatus 1310 is engaged with a male tapered part of the host structure. In some embodiments, a projecting male tapered part of the host structure can fit snugly into taper 1342 and can make a seal with taper 1342.

Fluidic optical cartridge 1310 also includes mating end 1350 that is configured to engage a pipettor tip. Both transparent optical region 1316 (that has transparent channel 1315 therewithin) and optical components 1320A and 1320B are fixed to base plate 1360. The optical components and the transparent optical region are in a fixed relationship with each other facilitating the use of the cartridge in the host structure since important optical alignments in the cartridge are molded into the piece.

Figure 14:
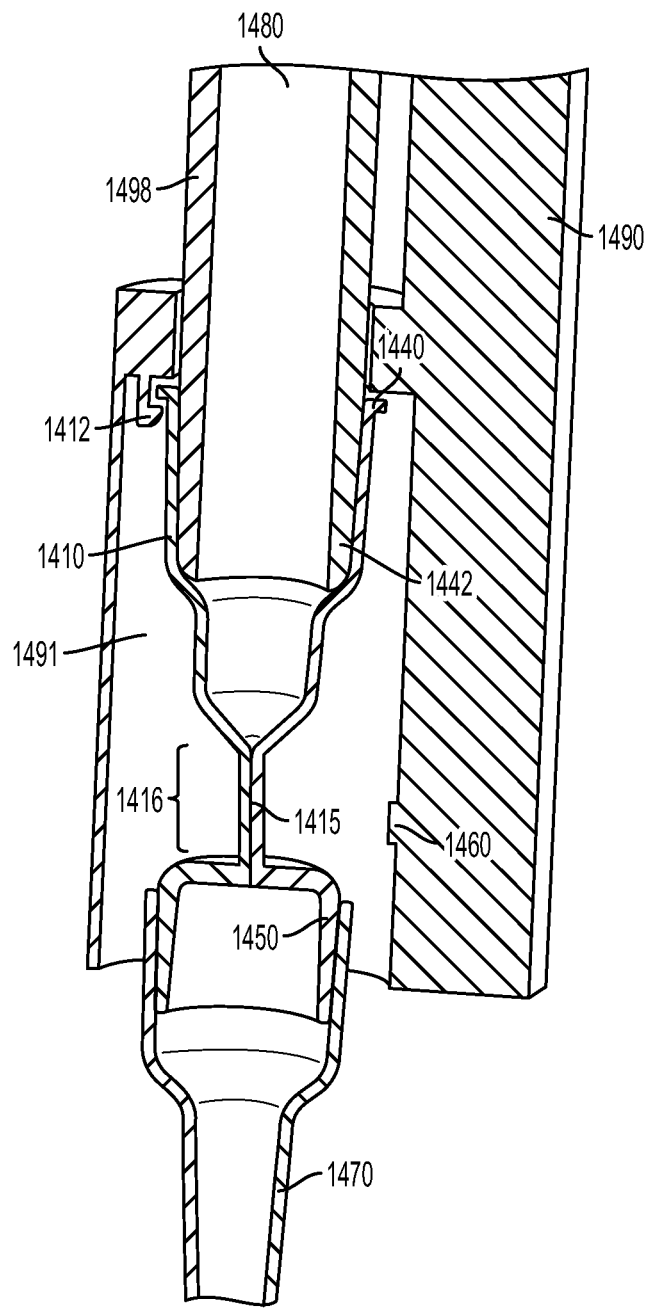
FIG. 14 is a cross-sectional cut-away view of an example embodiment of a fluidic optical cartridge engaged in a host structure.

FIG. 14 is a cross-sectional cut-away view of an example embodiment of an apparatus engaged in a host structure. In some embodiments, the apparatus can be a fluidic optical cartridge. Fluidic optical cartridge 1410 includes transparent optical region 1416 that has transparent channel 1415 therewithin. Fluidic optical cartridge 1410 also includes taper 1442 that has flange 1440 that is engaged with interlock tab 1412 of host structure 1490. Host structure 1490 is only partially shown in FIG. 14. Fluidic optical cartridge 1410 also has mating end 1450 that, in this embodied illustration, is mated to pipettor tip 1470. Optical components, that are also part of fluidic optical cartridge 1410 and are shown in FIGS. 8, 9, and 10A-10D are not shown in FIG. 14.

Host structure 1490 can lock with fluidic optical cartridge 1410 and hold itself into position with interlock tab 1412 and can, in an additional step, eject disposable fluidic optical cartridge 1410 from host structure 1490. Host structure 1490 also includes air cylinder 1480 inside of which an air piston (not shown in FIG. 14) snugly fits. Air cylinder 1480 is inside of shaft 1498 which makes an air-tight seal with fluidic optical cartridge 1410 when it is engaged with host structure 1490 as shown. Pipettor tip 1470 also makes an air-tight seal with mating end 1450 of fluidic optical cartridge 1410 as shown. Host structure 1490 also includes a waveguide that provides measurement light to waveguide portal 1460. Light emanating from waveguide portal 1460 impinges upon objects traveling through transparent channel 1415 in transparent optical region 1416 of fluidic optical cartridge 1410. The light may also interact with other optical components fixedly attached to fluidic optical cartridge 1410 as shown in FIGS. 8, 9, and 10A-10D.

Figure 15:
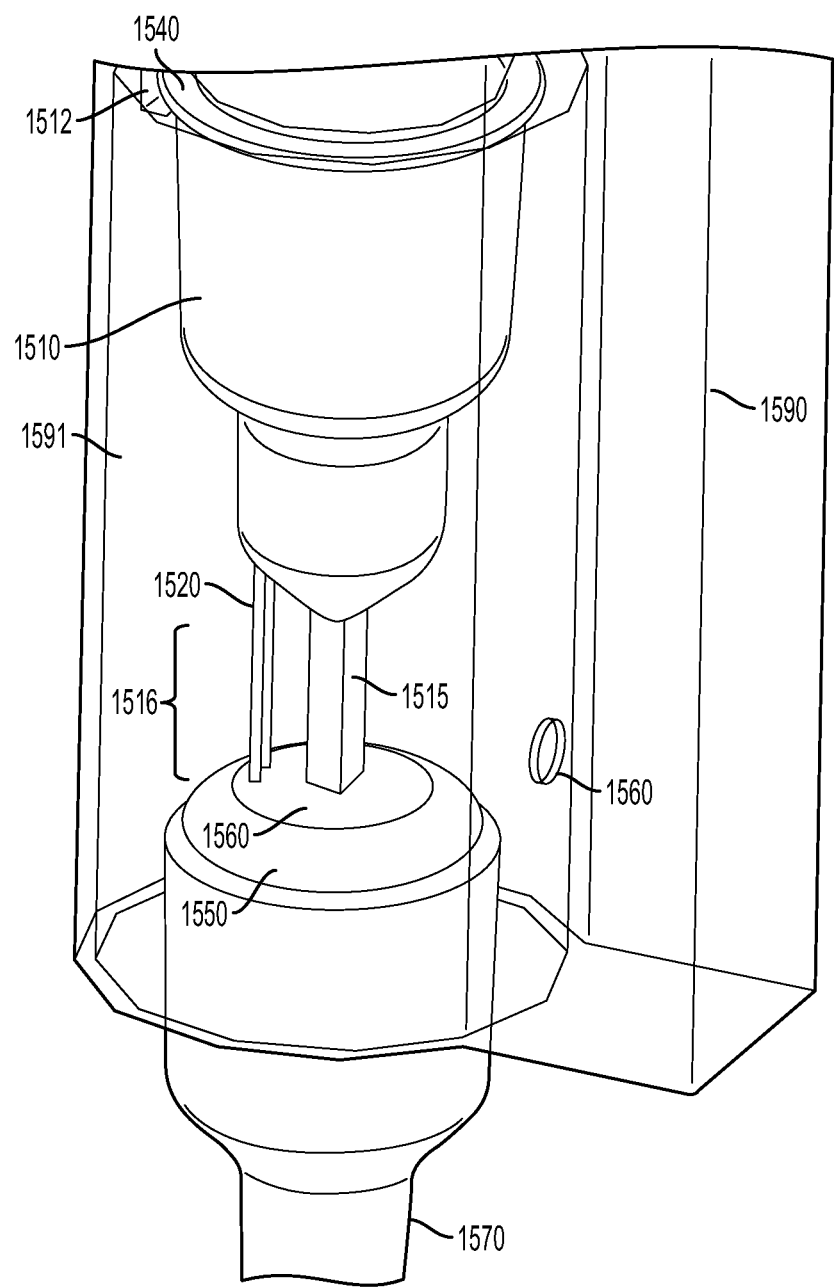
FIG. 15 is a see-through perspective drawing of an example embodiment of a fluidic optical cartridge engaged in a host structure.

FIG. 15 is a see-through perspective drawing of an example embodiment of an apparatus engaged in a host structure. In some embodiments, the apparatus can be a fluidic optical cartridge. Fluidic optical cartridge 1510 includes transparent optical region 1516 that has transparent channel 1515 therewithin. Fluidic optical cartridge 1510 also includes a taper that has flange 1540 that is engaged with interlock tab 1512 of host structure 1590. Host structure 1590 is only partially shown in FIG. 15. Fluidic optical cartridge 1510 also has mating end 1550 that, in this embodied illustration, is mated to pipettor tip 1570. Optical component 1520, that is also part of fluidic optical cartridge 1510, is also visible in FIG. 15.

Host structure 1590 can lock with fluidic optical cartridge 1510 and can, in an additional step, eject fluidic optical cartridge 1510 from host structure 1590. FIG. 15 is an illustration of host structure 1590 that includes fluidic optical cartridge 1510 that is in the "measure" mode. Host structure 1590 also includes a waveguide that provides measurement light to waveguide portal 1560. Measurement light emanating from waveguide portal 1560 impinges upon objects traveling through transparent channel 1515 in transparent optical region 1516 of fluidic optical cartridge 1510. Output light emanates from transparent optical region 1516 and can be detected by a detector (not shown) in host structure 1590.

Figure 16A:
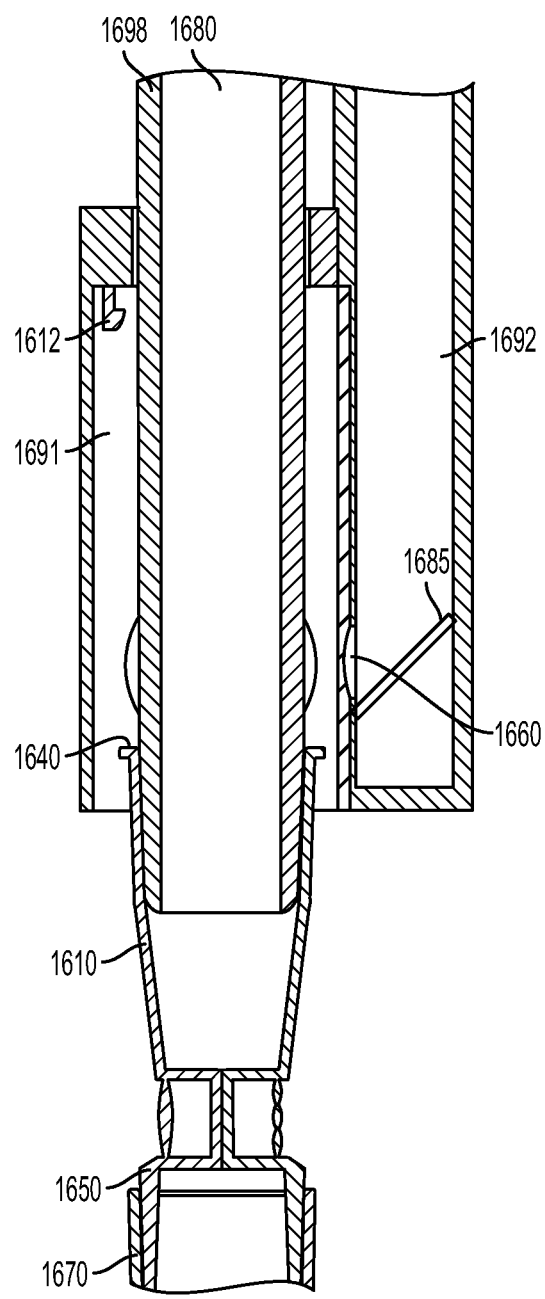
FIGS. 16A-16C are cross-sectional side views showing how the fluidic optical cartridge engages with the host structure.
Figure 16B:
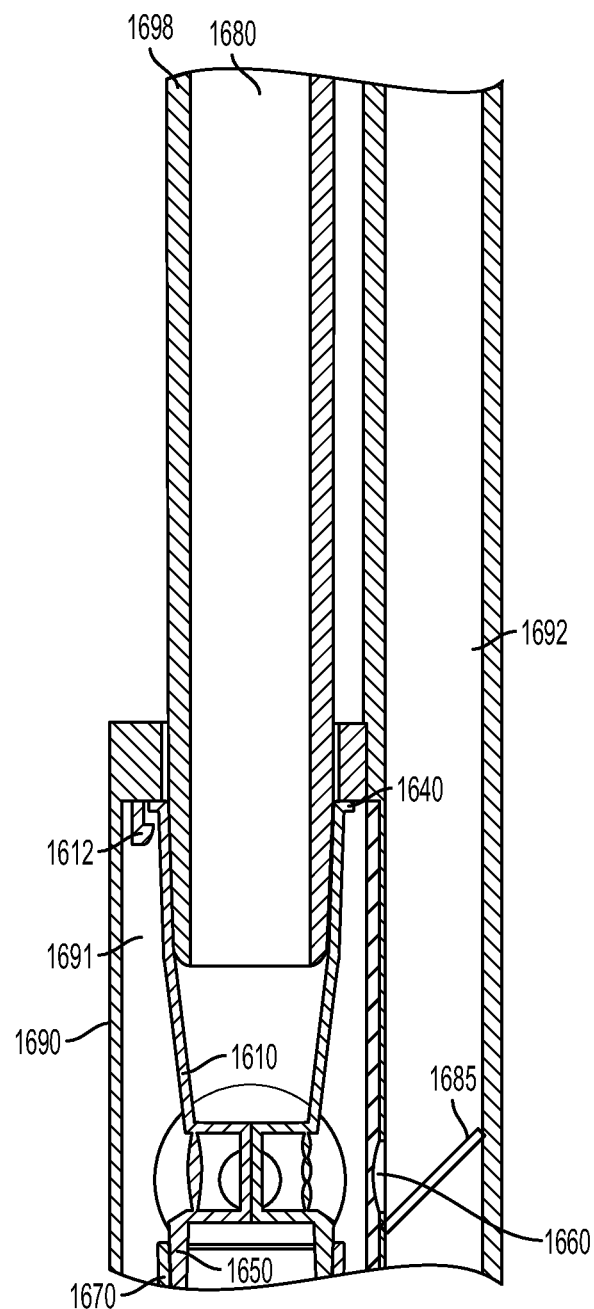
Figure 16C:
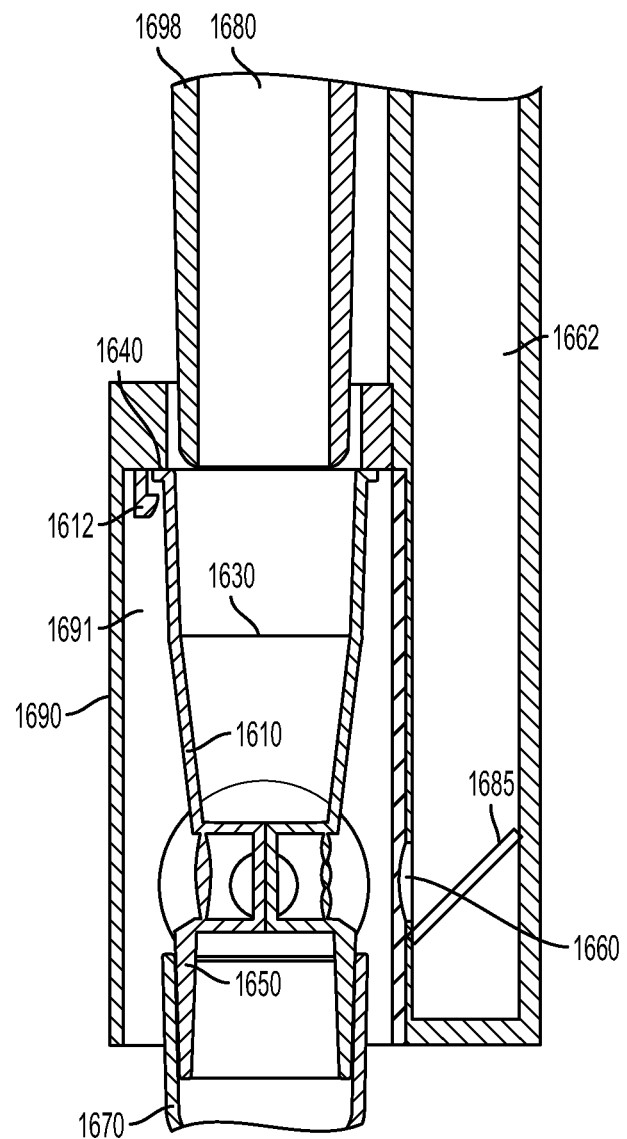

FIGS. 16A-16C are cross-sectional side views showing how the fluidic optical cartridge engages with the host structure. In FIG. 16A, fluidic optical cartridge 1610 is engaged in host structure 1690 in the "ready" mode. In the "ready" mode, disposable fluidic optical cartridge 1610 is at least partially within compartment 1691 of host structure 1690. Interlock tab 1612 is configured to interlock with flange 1640 with a snap fit to disposable fluidic optical cartridge 1610. In the illustration shown in FIGS. 16A-16C, host structure 1690 has only one interlock (snap fit) tab 1612. There may be more than one interlock tab but the interlock tabs, if present, are asymmetrically located around the perimeter of flange 1640 of disposable fluidic optical cartridge 1610 which facilitates ejection of the cartridge. FIG. 16A is an illustration of a portion of host structure 1690 and includes compartment 1619 which contains fluidic optical cartridge 1610 partially therewithin, shaft 1698 which is slideably engaged with host structure 1690, and waveguide 1692 which, in the embodiment illustrated in FIG. 16A, is a hollow tube with light-redirecting element 1685 which can redirect measurement light traveling down the hollow tube through waveguide portal 1660 to fluidic optical cartridge 1610. Waveguide 1692 is in mechanical or electromechanical communication with a button on the head of the host structure (see FIGS. 5-6). In the "ready" mode, the button shaft (not visible) and waveguide 1692 are in a neutral position where it is slideably engaged with host structure 1690, but not engaged with fluidic optical cartridge 1610 as shown in FIG. 16A. A spring (not shown) can provide resistance to the button shaft allowing it and the waveguide 1692 to return to the "ready" mode position when not depressed. Air cylinder 1680 is inside of shaft 1698 and is available for use when the flow cytometer is in the "measure" mode as will be illustrated in FIG. 16B. FIG. 16A also show mating end 1650 of fluidic optical cartridge 1610 engaged with pipettor tip 1670.

FIG. 16B is an illustration of fluidic optical cartridge 1610 within compartment 1691 of host structure 1690 in the "measure" mode. In the "measure" mode the button on the head of the host structure has been partially depressed so that the relative positions of shaft 1698, fluidic optical cartridge 1610, and waveguide 1692 are as shown. Shaft 1698 is engaged in optical fluidic cartridge 1610 and forms an air seal by engaging with tapered sides of optical fluidic cartridge 1610 and, in some embodiments, a button shaft stop (not shown in FIG. 16B). The downward force applied to button shaft also allows flange 1640 of fluidic optical cartridge 1610 to engage interlock tab 1612 and allowing a good air seal to form between air cylinder 1680 and the fluid (air or liquid analyte) within fluidic optical cartridge 1610. In some embodiments, a plunger is seated in air cylinder 1680 that is useful for providing a vacuum or pressure within the fluidic system that includes fluidic optical cartridge 1610 and, when attached, pipettor tip 1670.

When in the "measure" mode, the pipette partially illustrated in FIG. 16B can draw analyte fluid up into the measurement part of fluidic optical cartridge 1610 (described earlier) so that measurement light can be directed to the transparent channel in which objects in the analyte fluid are moving along their respective paths. In some embodiments, the flow of the analyte fluid through the transparent channel during the "measure" mode can be carefully controlled by pumps controlling a piston in air cylinder 1680. As discussed previously, output light emanating from objects in the analyte fluid can be captured by a detector either on the base plate of the fluidic optical cartridge or attached to the host structure. The measurement light, the output light, or both can pass through one or more filter assemblies that can be used, for example, to encode the measurement light and decode the output light so that, for example, spatial modulation analysis of properties of the objects in the analyte fluid can be performed. In other embodiments, other types of analyses are also possible using the apparatuses and methods described herein.

FIG. 16C is an illustration of the fluidic optical cartridge 1610 within compartment 1691 of host structure 1690 in the "eject" mode. To put the fluidic optical cartridge and host structure in the "eject" mode, the button on the head of the host structure is further depressed (beyond the amount of depression needed for the "measure" mode) so that button shaft pushes fluidic optical cartridge 1610 (with pipettor tip 1670) off shaft 1698 and past interlock tab 1612 thereby ejecting disposable fluidic optical cartridge 1610 (and pipettor tip 1670 when engaged with fluidic optical cartridge 1610). The presence of a single interlock tab 1612 that has engaged only one side of flange 1640 of fluidic optical cartridge 1610 or several interlock tabs asymmetrically placed around flange 1640 of fluidic optical cartridge 1610 allows fluidic optical cartridge 1610 to disengage from interlock tab 1612 when in the "eject" mode.

Figure 17:
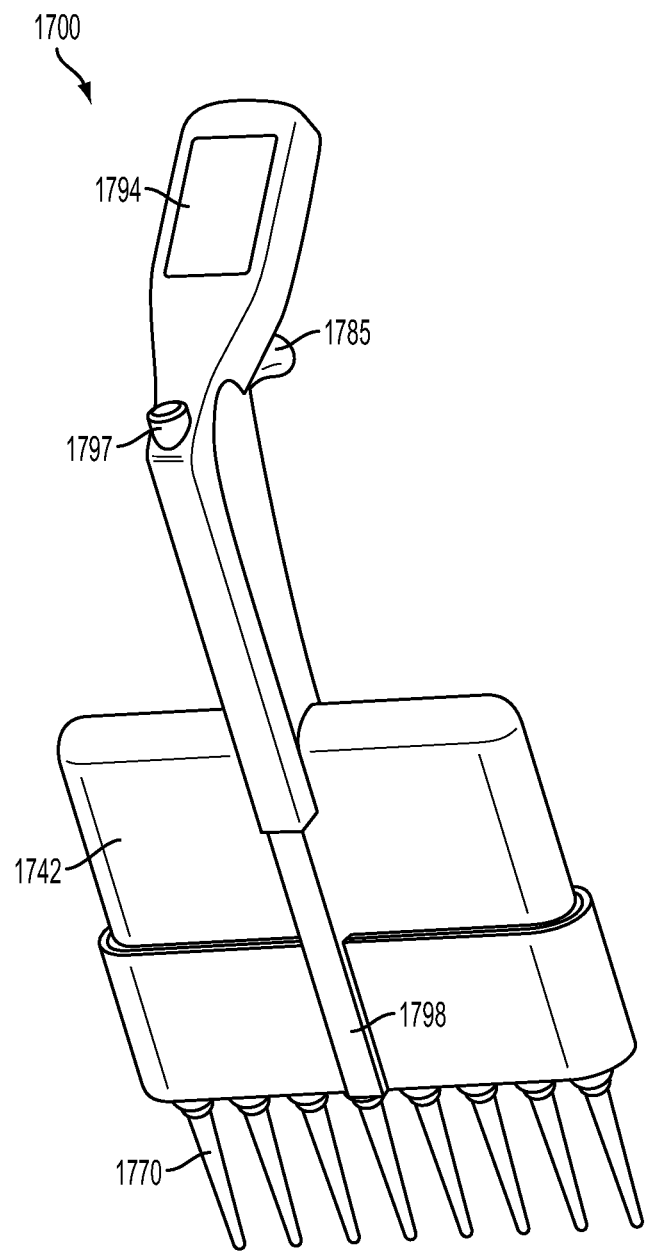
FIG. 17 is a perspective view of an embodiment of a fluidic optical cartridge engaged in a host structure having a manifold with multi-channel pipettor tips attached.

FIG. 17 is a perspective view of an embodiment of a disclosed flow cytometer in the "measure" mode having a manifold with multi-channel pipettor tips attached thereto. Flow cytometer 1700 includes display 1794, button 1979, button shaft 1798, and tapered manifold 1742. Multi-channel pipettor tip 1770 is engaged into tapered manifold 1742. Flow cytometer 1700 includes handle 1785 that is useful when the flow cytometer is used manually (hand-held).

Figure 18:
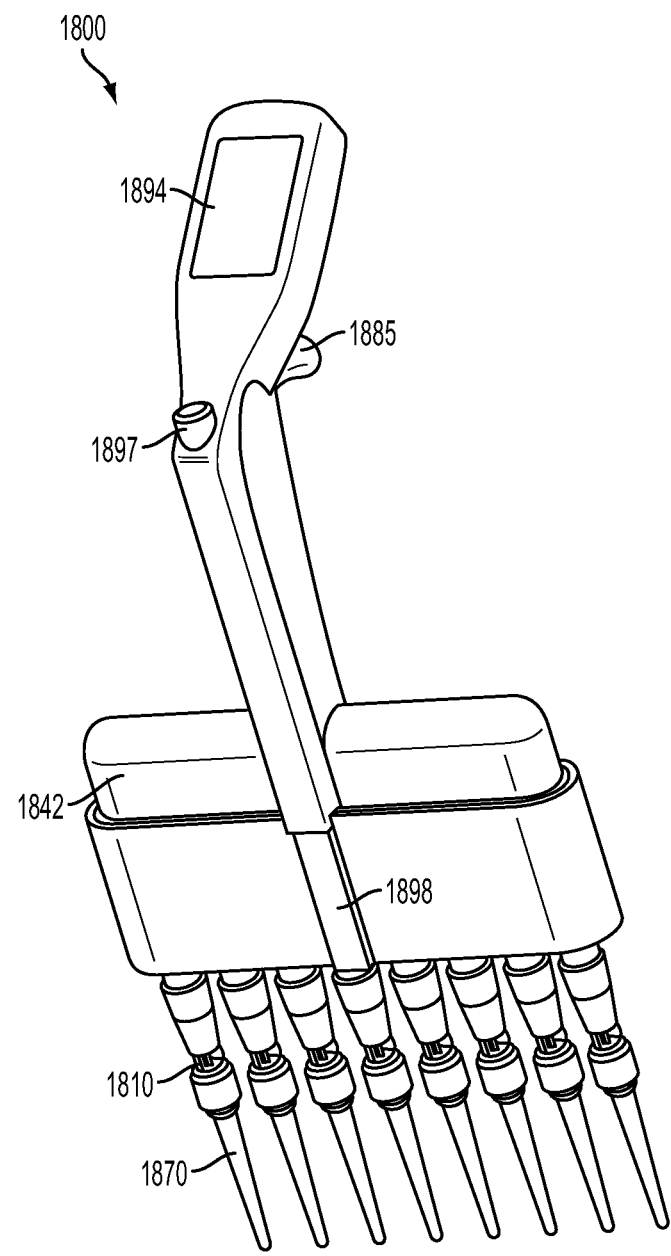
FIG. 18 is a perspective view of the embodiment shown in FIG. 17 in the "measure" mode.
Figure 19:
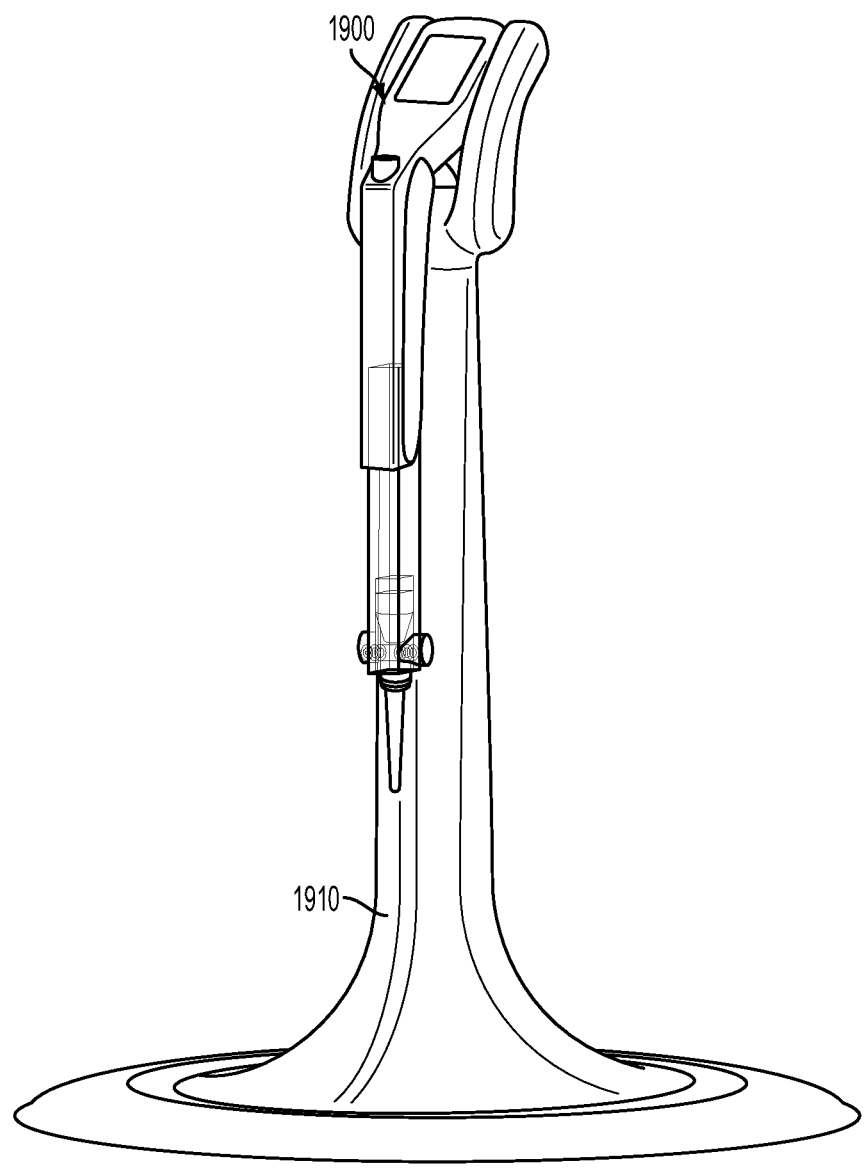
FIG. 19 is an illustration of a stand holding an embodiment of a fluidic optical cartridge engaged in a host structure according to the present disclosure.

FIG. 18 is a perspective view of the embodiment shown in FIG. 17 in the "ready" mode. In this view, flow cytometer 1800 includes display 1894, button 1897 which is in communication with button shaft 1898, and tapered manifold 1842. In the "ready" mode, button shaft 1898 is retracted exposing multichannel fluidic optical cartridge 1810 with pipettor tips 1870 attached. FIG. 19 is an illustration of a disclosed flow cytometer 1900 engaged in an embodiment of a stand when it is not in use. The disclosed flow cytometer (fluidic optical cartridge engaged at least partially within the disclosed host structure) can be operated by hand (sometimes even one hand), is portable, and is capable of point-of-care application. The flow cytometer can use disposable fluidic optical cartridges that can be molded or fabricated of transparent polymeric or other material. The important components of the optical path of the measurement light as it interacts with objects in an analyte fluid can be fixed in position on a base plate of the fluidic optical cartridge so no alignment of the measurement channel with the optical path is required. The fluidic cartridge is built in a way that light from the host structure overfills the acceptance area of the cartridge. For this reason, in some embodiments, only the transparent measuring channel and optical components that redirect measurement light and/or output light are fixed on the disposable fluidic optical cartridge. However, in some embodiments, other optical components such as filter assemblies, encoding components, decoding components, and detectors could possibly be molded to the base plate of the fluidic optical cartridge. The choice of optical components in the fluidic optical cartridge includes elements that provide time-varying light intensity signals of moving particles. The time pattern is correlated to the choice of optical component. For example, the pattern could be periodic for particles of constant speed.

One host structure can accept different fluidic optical cartridges. The characteristics of the fluidic optical cartridges can be transmitted to the evaluation electronics manually via, for example, a mechanical switch code or manual programming, or by automatic recognition via, for example, a barcode or radio-frequency identification detection (RFID) tag.

In another aspect, a method is disclosed that includes engaging a fluidic optical cartridge in a compartment of a host structure. The host structure can include a waveguide configured to deliver measurement light to a compartment at least partially within the host structure. The compartment can be configured to reversibly engage a fluidic optical cartridge. The host structure can also include a detector configured to receive the output light emanating from the compartment and electronics to process and/or analyze signals generated by the detector in response to the output light. The fluidic optical cartridge is described above and includes a fluidic structure that includes a transparent channel through which objects can travel along respective paths during operation of the apparatus and optical components configured to provide measurement light to the objects traveling through the transparent channel. The method further includes drawing analyte fluid into the fluidic structure and measuring properties of the objects in the fluid using measurement light. In some embodiments, the analyte fluid can be a biological fluid. In some embodiments, the concentration and/or presence of an analyte in a sample can be measured using an enzyme-reactive latent fluorophore attached to a support which, in some embodiments can be the object of analysis. Techniques that can use latent fluorophores linked to a support, and their use in assays are disclosed, for example, in co-owned U.S. patent application Ser. No. 13/826,198, entitled "Compositions and Methods for Performing Assays" (Recht et al.), filed Mar. 14, 2013 which is incorporated herein by reference in its entirety.

In some embodiments, absorption-encoded microbeads can be used in the disclosed flow cytometer for measuring characteristics of objects which, in some embodiments, can include the microbeads themselves. Alternatively the absorption-encoded microbeads can be used to analyze properties of a system such as, for example, one containing antibodies that bind specifically to certain antigens. Further disclosure of the use of absorption-encoded microbeads can be found, for example, in applicants' application, U.S. Ser. No. 13/627,739, entitled "Multiplexed Flow Assay Based On Absorption-encoded Micro Beads", (Kiesel et al.), filed Sep. 26, 2012. The use of multiple excitation sources is disclosed, for example, in applicants' application, U.S. Pat. App. Publ. No. 2013/0037726 (Kiesel et al.). These two disclosures are herein incorporated by reference in their entirety.

The disclosed method can also include ejecting the fluidic optical cartridge from the host structure. Ejecting the fluidic optical cartridge is particularly important if the fluidic optical cartridge is disposable. The method also can include outputting signals from the output light to a display, an analyzer, or both. The display, the analyzer, or both can be a part of the host structure or can be separate from the host structure. In some embodiments, the analyzer can output data (measured properties of the analyte fluid from the output light) over a wireless network such as a WiFi network.

Figure 20:
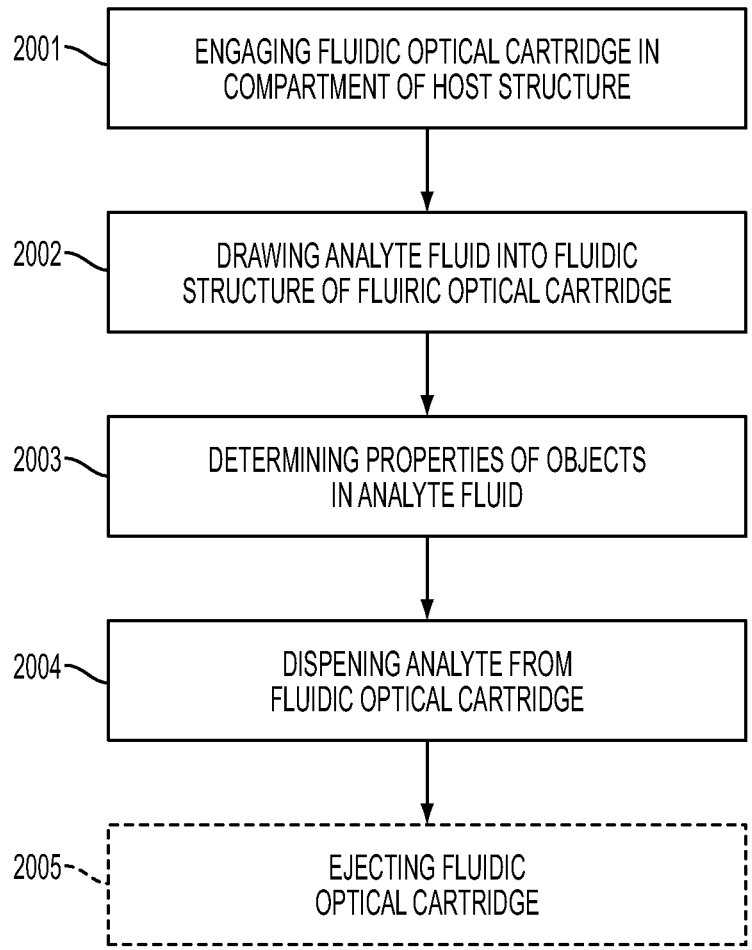
FIG. 20 is a flow diagram of disclosed methods.

FIG. 20 is a flow diagram of the basic method. The basic method includes engaging a fluidic optical cartridge in a compartment of a host structure (2001). The engaged fluidic optical cartridge can be used for drawing analyte fluid into a fluidic structure (transparent measurement channel) of the fluidic optical cartridge (2002). The method further includes measuring properties of the objects in the analyte fluid (2003). The method also includes dispensing analyte from the fluidic optical cartridge (2004). Optionally, the method can further include ejecting the fluidic optical cartridge (2005).

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. A host structure comprising:
   a compartment disposed at least partially within the host structure, the compartment being configured to reversibly engage with a fluidic optical cartridge, the compartment including an interlock feature configured to reversibly engage the fluidic optical cartridge, wherein the fluidic optical cartridge comprises:
   a fluidic structure that includes a channel through which objects can travel along respective paths during operation of the apparatus, the channel having at least one transparent wall; and at least one optical component configured to provide measurement light to the objects traveling through the channel, the output light emanating from the objects in response to the measurement light, the host structure further comprising a source of the measurement light;

a waveguide configured to deliver measurement light to the compartment;

a detector configured to receive output light emanating from the fluidic optical cartridge and to generate one or more electrical signals in response to the output light; and electronics to process the electrical signals from the detector.

2. A host structure according to claim 1, further comprising a handle.

3. A host structure according to claim 1, wherein the at least one optical component comprises a light-redirecting element that can redirect the measurement light from the host structure to the transparent channel of the fluidic structure.

4. A host structure according to claim 3, wherein the light-redirecting element comprises a lens, a lens array, a microlens array, a mirror, or a micromirror array.

5. A host structure according to claim 1, further comprising an analyzer configured to analyze the electrical signals from the detector to identify characteristics of the objects.

6. A host structure according to claim 1, wherein the electronics are configured to output data over a wireless network.

7. A host structure according to claim 1, further comprising a display.

8. A host structure according to claim 1, wherein the light source comprises a laser, a laser diode, a light-emitting diode, a superluminescent diode, a diode-pumped solid state laser, a frequency-doubled laser, a frequency-tripled laser, or a frequency-quadrupled laser.

9. A host structure according to claim 1, further comprising at least one filter assembly configured to provide encoding components to the measurement light emerging from the waveguide.

10. A host structure according to claim 1, further comprising at least one filter assembly configured to provide decoding components to the output light from the compartment.

11. A host structure according to claim 1, wherein the interlock feature comprises an interlock tab.

12. A host structure according to claim 1, wherein a button shaft mechanically or electromechanically connects a button on the host structure with the fluidic optical cartridge.

13. A host structure according to claim 12, wherein the button shaft is configured to allow the optical fluidic cartridged to measure properties of a fluidic sample.

14. A host structure according to claim 1, further comprising a button shaft configured to eject the fluidic optical cartridge from the compartment.

15. A host structure according to claim 1, wherein the fluidic optical cartridge is configured so that when the fluidic optical cartridge is engaged in the compartment a seal is made with the host structure.

16. A flow cytometer comprising a host structure according to claim 1, capable of analyzing objects in fluids.

17. A flow cytometer according to claim 16, wherein the weight of the flow cytometer is 1.0 kg or less.

18. A flow cytometer according to claim 16, wherein the volume of the flow cytometer is a component of the disclosed flow cytometer is 2 L or less.

19. A method comprising:

operating an interlock feature of a compartment of a host structure, operation of the interlock feature reversibly engaging a fluidic optical cartridge in the compartment of the host structure, wherein the host structure comprises:

a waveguide configured to deliver measurement light to a compartment at least partially within the host structure, the compartment being configured to reversibly engage a fluidic optical cartridge;

at least one detector configured to receive output light emanating from the compartment and to generate one or more electrical signals in response to the output light;

electronics configured to process the electrical signals, wherein the fluidic optical cartridge comprises:

a fluidic structure that includes a channel through which objects can travel along respective paths during operation of the apparatus, the channel having a transparent wall; and at least one optical component configured to provide the measurement light to the objects traveling through the channel;

drawing analyte fluid into the fluidic structure;

measuring characteristic properties of the objects in the fluid based on the electrical signals; and dispensing the analyte fluid from the fluidic structure.

20. A method according to claim 19, wherein the at least one optical component comprises a light-redirecting element that can redirect the measurement light from the host structure to the transparent channel of the fluidic structure.

21. A method according to claim 20, wherein the light-redirecting element comprises a lens, a lens array, a microlens array, a mirror, or a micromirror array.

22. A method according to claim 20 comprising using an enzyme-reactive latent fluorophore attached to a support.

23. A method according to claim 20 comprising the use of absorption-encoded microbeads.

24. A method according to claim 19, further comprising ejecting the fluidic optical cartridge from the host structure.

25. A method according to claim 19, further comprising outputting the characteristic properties of the objects to a display on the host structure.

26. A method according to claim 19, further comprising outputting the characteristic properties of the objects to an analyzer.

27. A method according to claim 26, wherein the outputting is over a wireless network.

* * * * *